(12) United States Patent
Shirai et al.

(10) Patent No.: US 9,678,187 B2
(45) Date of Patent: Jun. 13, 2017

(54) MAGNETIC RESONANCE IMAGING DEVICE, PHASE VALUE CORRECTION METHOD AND PROGRAM

(75) Inventors: Toru Shirai, Tokyo (JP); Yoshitaka Bito, Tokyo (JP); Satoshi Hirata, Tokyo (JP); Yoshihisa Soutome, Tokyo (JP)

(73) Assignee: Hitachi, Ltd., Tokyo (JP)

(*) Notice: Subject to any disclaimer, the term of this patent is extended or adjusted under 35 U.S.C. 154(b) by 672 days.

(21) Appl. No.: 14/240,171

(22) PCT Filed: Jul. 27, 2012

(86) PCT No.: PCT/JP2012/069238
§ 371 (c)(1),
(2), (4) Date: Apr. 23, 2014

(87) PCT Pub. No.: WO2013/027539
PCT Pub. Date: Feb. 28, 2013

(65) Prior Publication Data
US 2014/0306703 A1  Oct. 16, 2014

(30) Foreign Application Priority Data

Aug. 24, 2011 (JP) ................. 2011-183097

(51) Int. Cl.
*G01R 33/46* (2006.01)
*G01R 33/485* (2006.01)
*G01R 33/565* (2006.01)
*A61B 5/055* (2006.01)

(52) U.S. Cl.
CPC ....... *G01R 33/4625* (2013.01); *G01R 33/485* (2013.01); *G01R 33/56518* (2013.01); *A61B 5/055* (2013.01)

(58) Field of Classification Search
CPC .............. G01R 33/4625; G01R 33/485; G01R 33/56518; A61B 5/055
See application file for complete search history.

(56) References Cited

U.S. PATENT DOCUMENTS

| 8,258,785 B2 | 9/2012 | Hirata et al. |
| 2010/0013481 A1 | 1/2010 | Hirata et al. |
| 2011/0182495 A1* | 7/2011 | Sun ............. G06T 7/0004 382/141 |

FOREIGN PATENT DOCUMENTS

| WO | 2008087822 A1 | 7/2008 |
| WO | 2010137516 A1 | 12/2010 |

OTHER PUBLICATIONS

Machine translation of reference Shirai et al. (WO Pub No. 2010/137,516 A), Listed in IDS, Pub Date Dec. 2, 2010.*
A. W. Simonetti, et al., "Automated correction of unwanted phase jumps in reference signals which corrupt MRSI spectra after eddy current correction", Journal of Magnetic Resonance 2002 vol. 159, p. 151-p. 157.

(Continued)

*Primary Examiner* — Rodney Bonnette
(74) *Attorney, Agent, or Firm* — Brundidge & Stanger, P.C.

(57) ABSTRACT

An object of the present invention is to suppress artifacts generated by correction of spectral distortion induced by eddy currents in MRI devices with a simple method, and thereby improve accuracy of the correction.

11 Claims, 17 Drawing Sheets

(56) References Cited

OTHER PUBLICATIONS

Y. Pang, et al, "A New Post-processing Method to Remove Ringing Artifacts in Clinical MR Spectra", Proc. Intl. Soc. Mag. Reson. Med. 2007, p. 1378.
U. Klose et al., "In Vivo Proton Spectroscopy in Presence of Eddy Currents" Magnectic Resonance in Medicine 14, 26-30 (1990).
J. M. Wild, "Artifacts Introduced by Zero Order Phase Correction in Proton NMR Spectrocopy and a Method of Elimination by Phase Filtering" pgs., Journal of Magnetic Resonance 137, 430-436, 1999.
International Search Report from International Application No. PCT/JP12/069238 mailed Aug. 21, 2012.
International Preliminary Report on Patentabilty corresponding application No. PCT/JP2012/069238 reported on Feb. 25, 2014.

\* cited by examiner

100

120

130

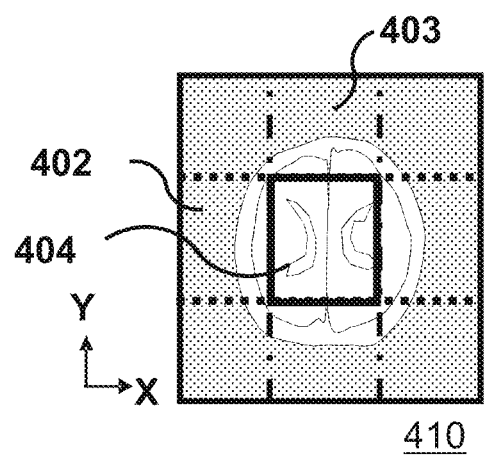
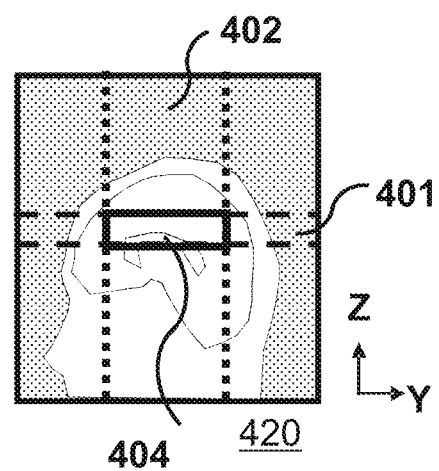
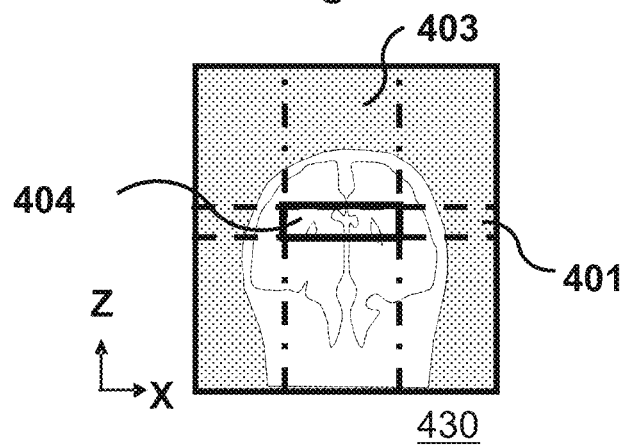

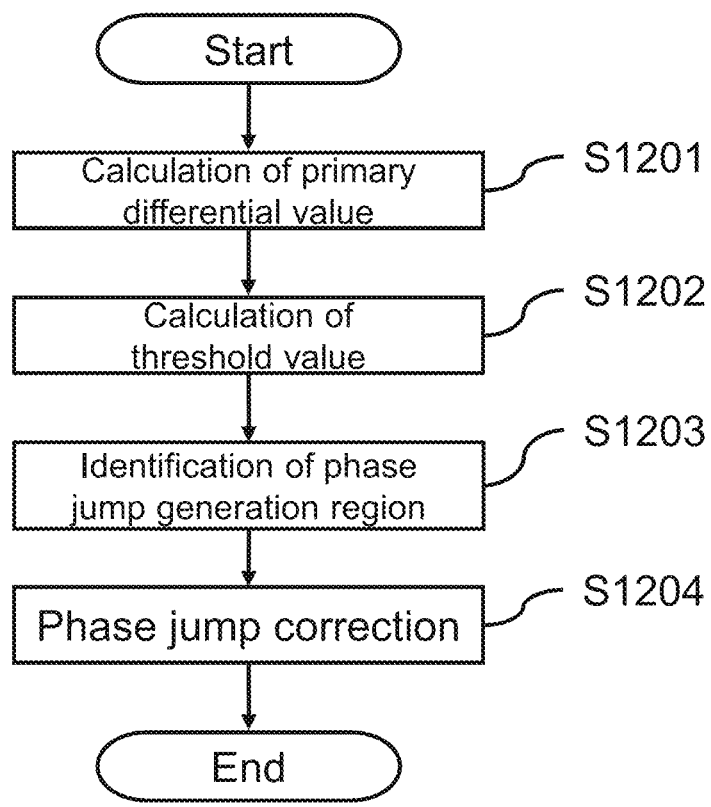

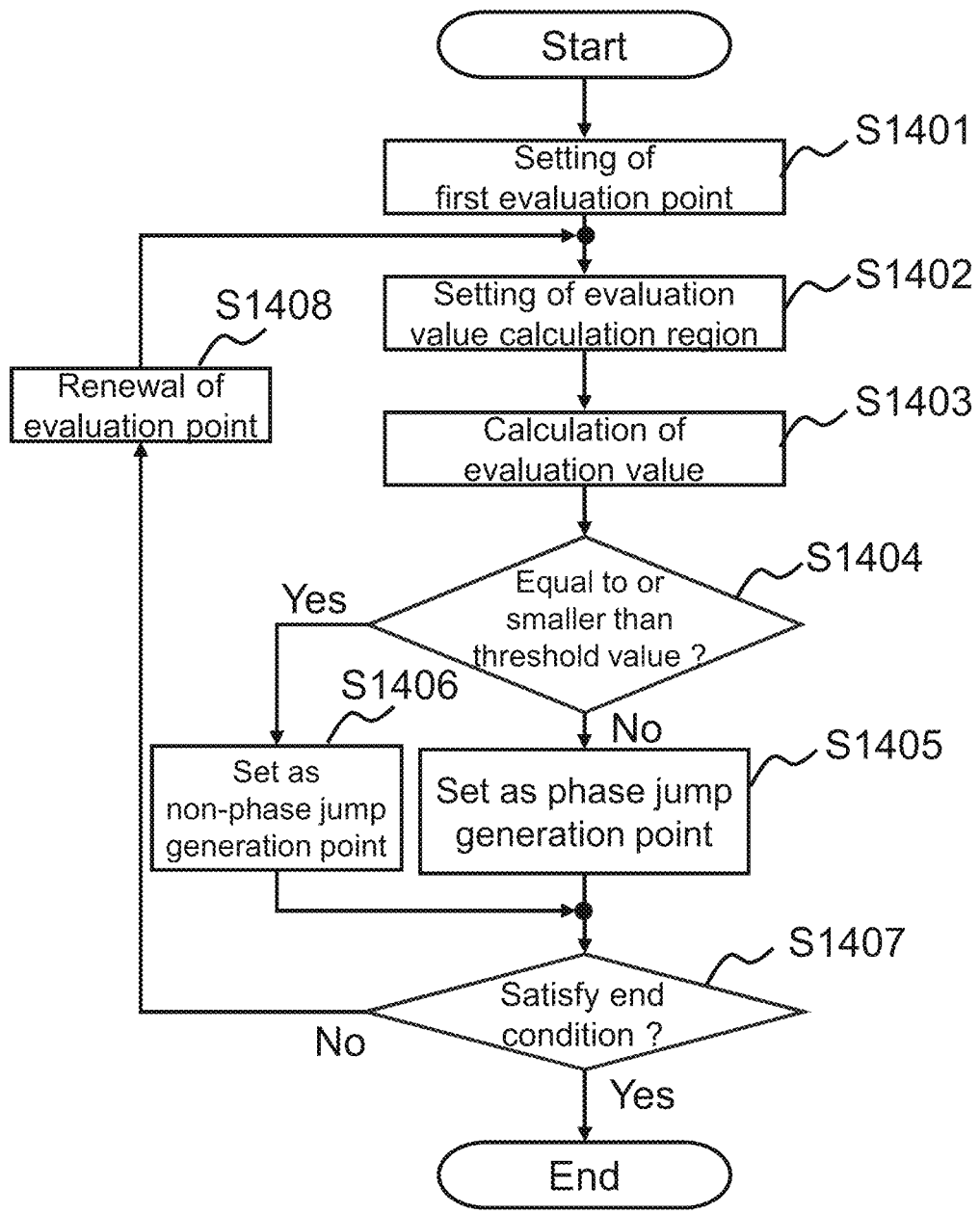

MAGNETIC RESONANCE IMAGING DEVICE, PHASE VALUE CORRECTION METHOD AND PROGRAM

TECHNICAL FIELD

The present invention relates to spectroscopic imaging, especially an eddy current correction technique therefor for correcting spectral distortion induced by eddy current and so forth.

BACKGROUND ART

In magnetic resonance signals measured in MRI, there is observed the chemical shift phenomenon, which means small differences of resonance frequency originated in difference in molecular structure. There are known MRS (Magnetic Resonance Spectroscopy), in which magnetic resonance signals are separated for every molecule (metabolite) by using the chemical shift phenomenon to obtain spectra, as well as CSI (Chemical Shift Imaging) and MRSI (Magnetic Resonance Spectroscopic Imaging), in which spatial signal intensity distribution is imaged for every metabolite.

Major metabolites of human bodies detectable by MRS or MRSI include choline (Cho), creatine (Cr), N-acetylaspartic acid (NAA), lactic acid (Lac), and so forth. Amounts of these metabolites enable stage determination and early diagnosis of metabolic disorders such as cancers. Moreover, it is also considered that they enable noninvasive diagnosis of malignancy of tumors.

In MRS and MRSI, eddy currents are induced by gradient magnetic fields applied at the time of measurement. Eddy currents cause spatially and temporally uneven static magnetic fields to distort shapes of spectra obtained by the measurement. This spectral distortion is usually corrected by using phase values of signals of a substance showing higher signal intensities compared with metabolites. For example, water is used as the substance showing higher signal intensities compared with metabolites (refer to, for example, Non-patent document 1). According to the method disclosed in Non-patent document 1, spatial and temporal phase values are calculated from FID (Free Induction Decay) signals of water, and phase correction is performed for metabolite image data to correct the spectral distortions induced by eddy currents.

In CSI or MRSI, size of measurement matrix (voxel number) is very small, as small as about 8×8 to 32×32, in view of measurement time and SNR (signal to noise ratio). Therefore, truncation is caused by the Fourier transform performed in the image reconstruction to cause contamination of signals of distant voxels. As a result, unevenness of static magnetic field causes contamination of water signals having a frequency different from that of the water signals in the objective voxels.

Contamination of water signals of such a different frequency generates so-called phase jump regions in time change of the phase values used for the eddy current correction. The phase jump regions are regions where variations of change amounts of phase values per unit time are outstandingly larger compared with the other regions. Magnitude of the phase value change in the phase jump regions is proportional to concentration of the contaminated water signals. Such phase jump will be explained below with reference to FIG. 17.

FIG. 17A shows water signal spectra obtained by computer simulation. The curves of Water 1 and Water 2 shown in FIG. 17A represent spectra of water signals having frequencies of 2 Hz and 5 Hz, respectively, and a concentration ratio of 1.0:0.9. Temporal change of phase value of the FID signal of water in the time domain in the presence of these two kinds of signals is shown in FIG. 17B. As shown in FIGS. 17A and 17B, when the frequency difference is $\Delta f$, there are generated phase jumps proportional to the concentration ratio with a time interval of $1/\Delta f$. In this example, mild phase change is induced by adding static magnetic field change caused by an eddy current.

Spectra obtained before and after performing correction of spectral distortion caused by eddy currents of metabolites using phase values showing the change shown in FIG. 17B for the time direction are shown in FIGS. 17C and 17D, respectively. The spectrum observed before the eddy current correction is shown in FIG. 17C, and the spectrum obtained after the eddy current correction is shown in FIG. 17D. As shown in FIG. 17D, if the correction is performed by using phase values including phase jumps, ringing artifacts are generated by the phase jumps, and thus the spectrum is degraded by the eddy current correction to the contrary.

As a countermeasure for the above problem, there is, for example, a method of reducing ringing artifacts by passing the spectrum of water signal through a low pass filter (refer to, for example, Non-patent document 2). There is also a method of reducing ringing artifacts by correcting phase jumps observed in phase values of FID signals of water (refer to, for example, Non-patent document 3). In Non-patent document 3, points of extremes of intensities as absolute values of the FID signals of water within a time domain are considered as a phase jump generation region. Further, the ranges to be removed as phase jumps are determined by using a primary derivative for time t of the phase values of the FID signals of water. Specifically, they are determined by fitting regions of the primary derivative around the aforementioned phase jump generation region with a model function, and using full widths at half maximum (FWHM) of the model function obtained by the fitting. Then, correction of phase values of the determined ranges is performed for the phase values.

PRIOR ART REFERENCES

Non-Patent Documents

Non-patent document 1: Uwe Klose, "In Vivo Proton Spectroscopy in Presence of Eddy Currents", Magnetic Resonance In Medicine, vol. 14, pp. 26-30 (1990)

Non-patent document 2: J. M. Wild, "Artifacts Introduced by Zero Order Phase Correction in Proton NMR Spectroscopy and a Method of Elimination by Phase Filtering", Journal of Magnetic Resonance, vol. 137, pp. 430-436 (1999)

Non-patent document 3: A. W. Simonetti, et al., "Automated correction of unwanted phase jumps in reference signals which corrupt MRSI spectra after eddy current correction", Journal of Magnetic Resonance, vol. 159, pp. 151-157 (2002)

DISCLOSURE OF THE INVENTION

Object to be Achieved by the Invention

However, even if the method of Non-patent document 2 is used, low frequency components of phase jumps remain, and therefore the ringing artifacts cannot be completely removed. Moreover, since radio frequency components of eddy currents are cut, sufficient effect of eddy current correction cannot be obtained.

With the method described in Non-patent document 3, phase jumps generated in spite of the absence of extremes of intensities as absolute value of the FID signals of water in the time domain cannot be corrected. Further, when there are a plurality of sharp phase changes, it is difficult to identify and extract the phase jump regions from them. Further, when there are a plurality of phase jumps of different phase change amounts, in order to enhance fitting accuracy, it is necessary to perform the fitting for every phase jump generation region, and thus the processing comes to be complicated. Furthermore, although the ranges for correcting phase jumps are determined in terms of primary differential values, the correction itself is performed in terms of phase values. Therefore, it is necessary to determine the phase change amounts of the correction regions in accordance with temporal changes of the phase values, and perform the correction so that the correction regions and the other regions are smoothly connected, and thus the processing comes to be complicated.

The present invention was accomplished in light of the aforementioned circumstances, and an object of the present invention is to suppress artifacts generated by correction of spectral distortion induced by eddy currents in MRI devices with a simple method, and thereby improve accuracy of the correction.

Means for Achieving the Object

According to the present invention, in the eddy current correction processing for correcting spectral distortion caused by an eddy current using phase values of FID signals of a substance showing higher signal intensities compared with a metabolite as an object of measurement, phase jumps of the phase values used for the correction are corrected beforehand. In the correction of the phase jumps, small phase change amount regions are first identified by using primary time differential values of the phase values, and the other regions are identified as phase jump generation regions. Then, the primary time differential values corresponding to the identified phase jump generation regions are excluded. The phase jump generation region is identified as a region where the primary time differential value changes in an amount not smaller than a threshold value defined beforehand within a range defined beforehand.

Specifically, the present invention provides a magnetic resonance imaging device comprising a static magnetic field application part for applying a static magnetic field to a subject, a gradient magnetic field application part for applying a gradient magnetic field to the subject, a radio frequency magnetic field pulse irradiation part for irradiating a radio frequency magnetic field pulse on the subject, a reception part for receiving magnetic resonance signals generated from the subject, and a control part, wherein the control part comprises a measurement control part for controlling operations of the gradient magnetic field application part, the radio frequency magnetic field pulse irradiation part, and the reception part to obtain a magnetic resonance signal of a desired metabolite for every measurement point, an eddy current correction part for performing eddy current correction of the magnetic resonance signal, and a display information generation part for generating display information from the magnetic resonance signal for every measurement point corrected by the eddy current correction part, the eddy current correction part comprises a phase value calculation part for calculating a phase value of an FID signal of a substance for correction showing a larger signal intensity compared with a metabolite as a measurement object for every measurement point, and a phase value correction part for correcting a phase jump of the phase value to obtain a corrected phase value, the phase value correction part comprises a primary differential value calculation part for calculating a primary time differential value of the phase value for every measurement point, a threshold value calculation part for calculating a threshold value for identifying a phase jump generation region where a phase jump is generated, a phase jump generation region identification part for identifying the phase jump generation region of the phase value using the threshold value and the primary time differential value, and a phase jump correction part for correcting the phase jump of the phase value by correcting the primary time differential value of the phase jump generation region, and the eddy current correction part performs the eddy current correction by using the phase jump-corrected phase value.

The present invention also provides a phase value correction method for correcting a phase jump of a phase value in a magnetic resonance imaging device comprising a static magnetic field application part for applying a static magnetic field to a subject, a gradient magnetic field application part for applying a gradient magnetic field to the subject, a radio frequency magnetic field pulse irradiation part for irradiating a radio frequency magnetic field pulse on the subject, a reception part for receiving magnetic resonance signals generated from the subject, a measurement control part for controlling operations of the gradient magnetic field application part, the radio frequency magnetic field pulse irradiation part, and the reception part to obtain a magnetic resonance signal of a desired metabolite for every measurement point, an eddy current correction part for performing eddy current correction of the magnetic resonance signal by using a phase value of an FID signal of a substance for correction showing a larger signal intensity compared with a metabolite as a measurement object for every measurement point, and a display information generation part for generating display information from the magnetic resonance signal for every measurement point corrected by the eddy current correction part, which comprises a primary differential value calculation step of calculating a primary time differential value of the phase value for every measurement point, a threshold value calculation step of calculating a threshold value for identifying a phase jump generation region where a phase jump is generated, a phase jump generation region identification step of identifying the phase jump generation region of the phase value using the threshold value and the primary time differential value, a phase jump correction step of correcting the phase jump of the phase value by correcting the primary time differential value of the phase jump generation region, and a corrected phase value calculation step of obtaining a corrected phase value from the corrected primary time differential value.

The present invention also provides a program for operating a computer of a magnetic resonance imaging device comprising a static magnetic field application part for applying a static magnetic field to a subject, a gradient magnetic field application part for applying a gradient magnetic field to the subject, a radio frequency magnetic field pulse irradiation part for irradiating a radio frequency magnetic field pulse on the subject, a reception part for receiving magnetic resonance signals generated from the subject, a measurement control part for controlling operations of the gradient magnetic field application part, the radio frequency magnetic field pulse irradiation part, and the reception part to obtain a magnetic resonance signal of a desired metabolite for every measurement point, an eddy current correction part for performing eddy current correction of the magnetic resonance signal by using a phase value of an FID signal of a substance for correction showing a larger signal intensity compared with a metabolite as a measurement object for every measurement point, and a display information generation part for generating display information from the magnetic resonance signal for every measurement point corrected by the eddy current correction part, as a primary differential value calculation part for calculating a primary time differential value of the phase value for every measurement point, a threshold value calculation part for calculating a threshold value for identifying a phase jump generation region where a phase jump is generated, a phase jump generation region identification part for identifying the phase jump generation region of the phase value using the threshold value and the primary time differential value, and a phase jump correction part for correcting the phase jump of the phase value by correcting the primary time differential value of the phase jump generation region and obtaining a corrected phase value from the corrected primary time differential value.

Effect of the Invention

According to the present invention, in the correction of spectral distortion caused by an eddy current in an MRI device, artifacts generated by the correction can be suppressed by a simple method to improve accuracy of the correction.

BRIEF DESCRIPTION OF THE DRAWINGS

FIG. 6A is a drawing for explaining a region excited by the MRSI pulse sequence according to one embodiment of the present invention.

FIG. 6B is a drawing for explaining a region excited by the MRSI pulse sequence according to one embodiment of the present invention.

FIG. 6C is a drawing for explaining a region excited by the MRSI pulse sequence according to one embodiment of the present invention.

FIG. 7 is a flowchart of a phase value correction processing according to one embodiment of the present invention.

FIG. 11 is a flowchart of a phase jump generation region identification processing according to one embodiment of the present invention.

MODES FOR CARRYING OUT THE INVENTION

Hereafter, embodiments of the present invention will be explained. In all the drawings for explaining the embodiments, components having the same functions are indicated with the same numerals, and repetitive explanations thereof are omitted.

Figure 1A:
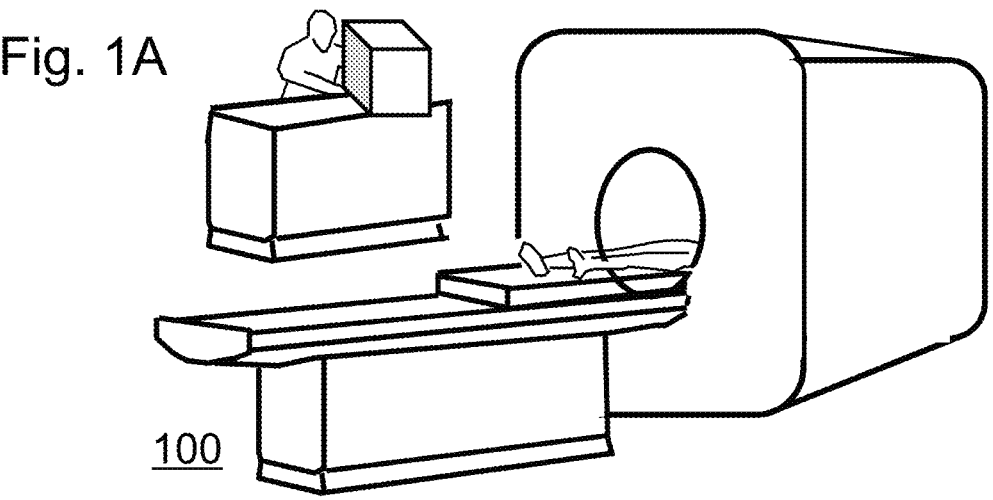
FIG. 1A is an exterior view of one embodiment of the magnetic resonance imaging device of the present invention.
Figure 1B:
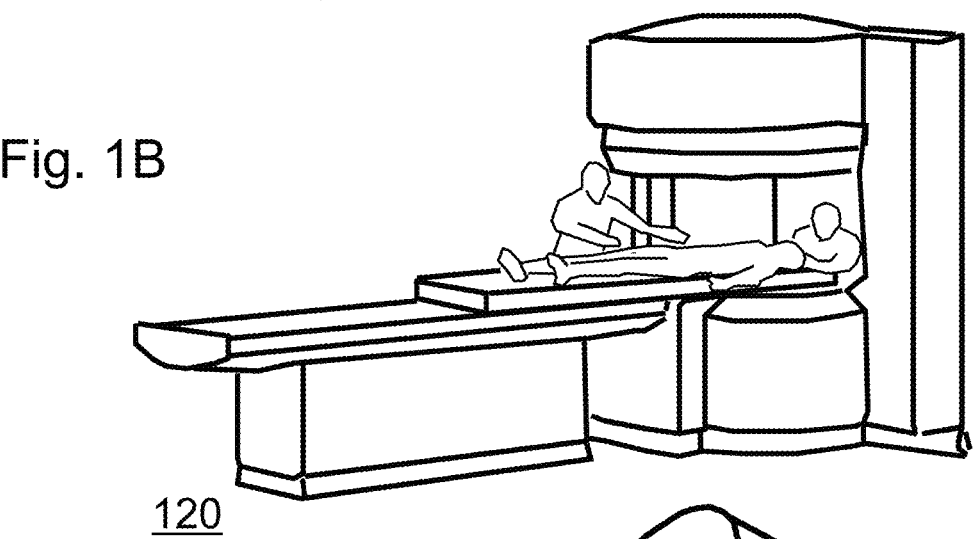
FIG. 1B is an exterior view of one embodiment of the magnetic resonance imaging device of the present invention.
Figure 1C:
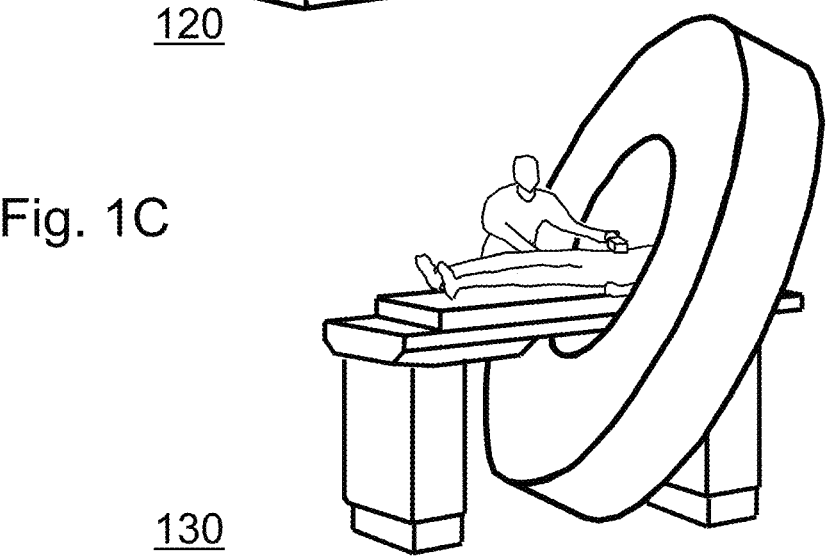
FIG. 1C is an exterior view of one embodiment of the magnetic resonance imaging device of the present invention.

First, magnetic resonance imaging devices (MRI devices) according to this embodiment of the present invention will be explained. FIGS. 1A to 1C are exterior views of MRI devices according to this embodiment. FIG. 1A shows an MRI device 100 of the horizontal magnetic field type utilizing a tunnel-shaped magnet that generates a static magnetic field with a solenoid coil. FIG. 1B shows an MRI device 120 of the vertical magnetic field type utilizing a hamburger type (open type) magnet having separated upper and lower magnets, which are used for increasing spaciousness. Further, FIG. 1C shows an MRI device 130 utilizing a tunnel-shaped magnet similar to that shown in FIG. 1A, but depth of the magnet is shortened and the magnet is leaned to increase spaciousness. For this embodiment, any of MRI devices having these exterior views can be used. These are mere examples, and the MRI device according to this embodiment is not limited to devices having these forms. For this embodiment, various kinds of known MRI devices can be used regardless of form or type thereof. In the following descriptions, the MRI device 100 will be explained as a typical example, unless it is especially necessary to distinguish those devices.

Figure 2:
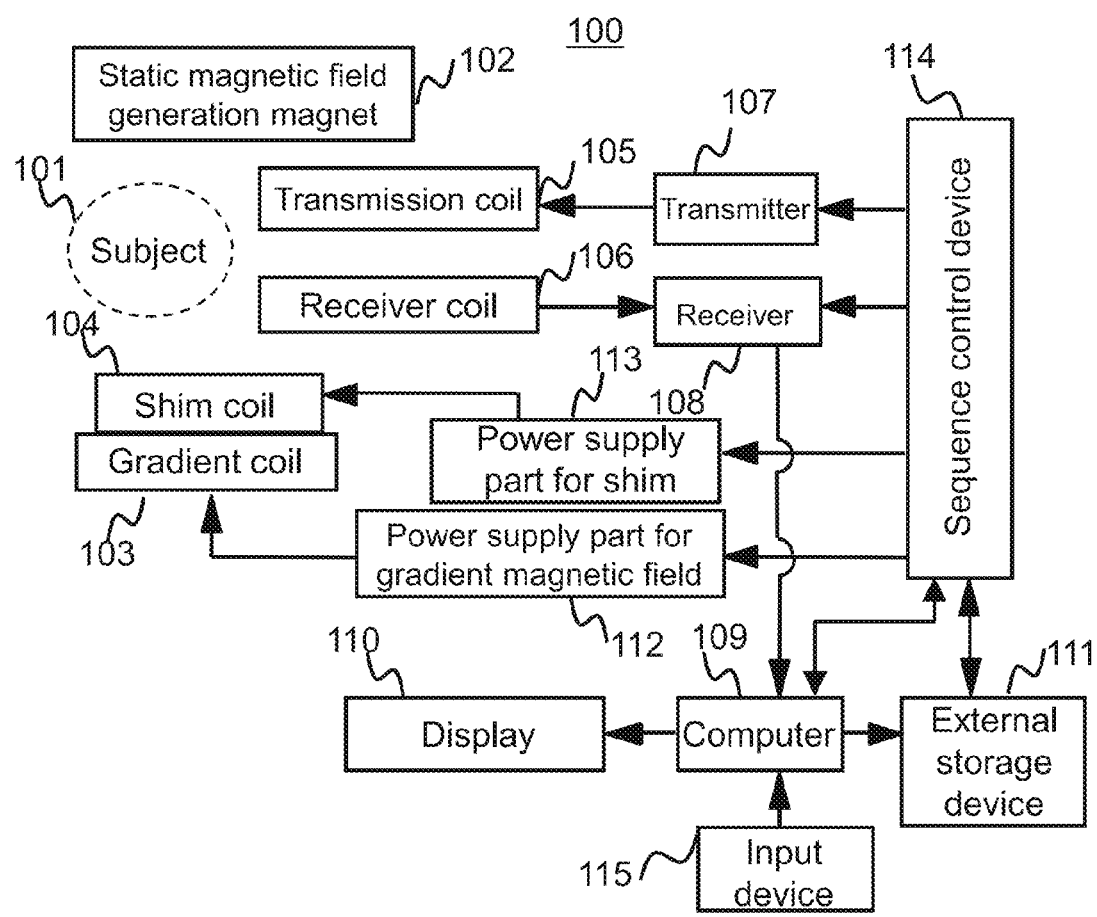
FIG. 2 is a functional configurational diagram of one embodiment of the nuclear magnetic resonance imaging device according to the present invention.

FIG. 2 is a functional configurational diagram of the MRI device 100 according to this embodiment. As shown in this drawing, the MRI device 100 according to this embodiment is provided with a static magnetic field generation magnet 102, which is the static magnetic field application part for applying a static magnetic field to a space in which a subject 101 is placed, a gradient coil 103, which is the gradient magnetic field application part for generating gradient magnetic fields in x-direction, y-direction, and z-direction, and applying the gradient magnetic fields to the subject, a shim coil 104 for adjusting static magnetic field distribution, a radio frequency coil 105 for measurement, which is the radio frequency magnetic field pulse irradiation part for irradiating a radio frequency magnetic field pulse on a measurement region of the subject 101 (henceforth simply referred to as transmission coil), a radio frequency coil 106 for reception, which is the reception part for receiving magnetic resonance signals generated from the subject 101 (henceforth simply referred to as reception coil), a transmitter 107, a receiver 108, a computer 109, a power supply part 112 for gradient magnetic field, a power supply part 113 for shim, and a sequence control device 114.

The static magnetic generation magnet 102 is chosen from those having various forms according to the structures of the MRI devices 100, 120 and 130 shown in FIGS. 1A, 1B and 1C, respectively. The gradient coil 103 and the shim coil 104 are driven by the power supply part 112 for gradient magnetic field and the power supply part 113 for shim, respectively. Although explanations of this embodiment will be made for a case of using the transmission coil 105 and the reception coil 106 as separate components, one coil serving as both the transmission coil 105 and the reception coil 106 may also be used. The radio frequency magnetic field irradiated by the transmission coil 105 is generated by the transmitter 107. The magnetic resonance signals detected by the reception coil 106 are sent to the computer 109 via the receiver 108.

The sequence control device 114 controls operations of the power supply part 112 for gradient magnetic field as the power supply for driving the gradient coil 103, the power supply part 113 for shim as a power supply for driving the shim coil 104, the transmitter 107, and the receiver 108 to control the timings of applications of the gradient magnetic fields and the radio frequency magnetic field, and reception of the magnetic resonance signals. The time chart of the control is called pulse sequence, which is set beforehand according to the measurement, and stored in a storage device or the like provided in the computer 109 described later.

The computer 109 is a controller for performing various kinds of processings for received magnetic resonance signals, generating image information and spectrum information, and controlling operations of the whole MRI device 100. The computer 109 is an information processor having CPU, memory, storage device, and so forth, and a display 110, an external storage device 111, an input device 115, and so forth are connected to the computer 109. The display 110 is an interface for displaying results obtained by processings and so forth for an operator. The input device 115 is an interface for the operator to input conditions, parameters and so forth required for the processings performed in this embodiment. The external storage device 111 stores data used for various kinds of processings executed by the computer 109, data obtained by the processings, inputted conditions, parameters, and so forth, together with the storage device.

Figure 3:
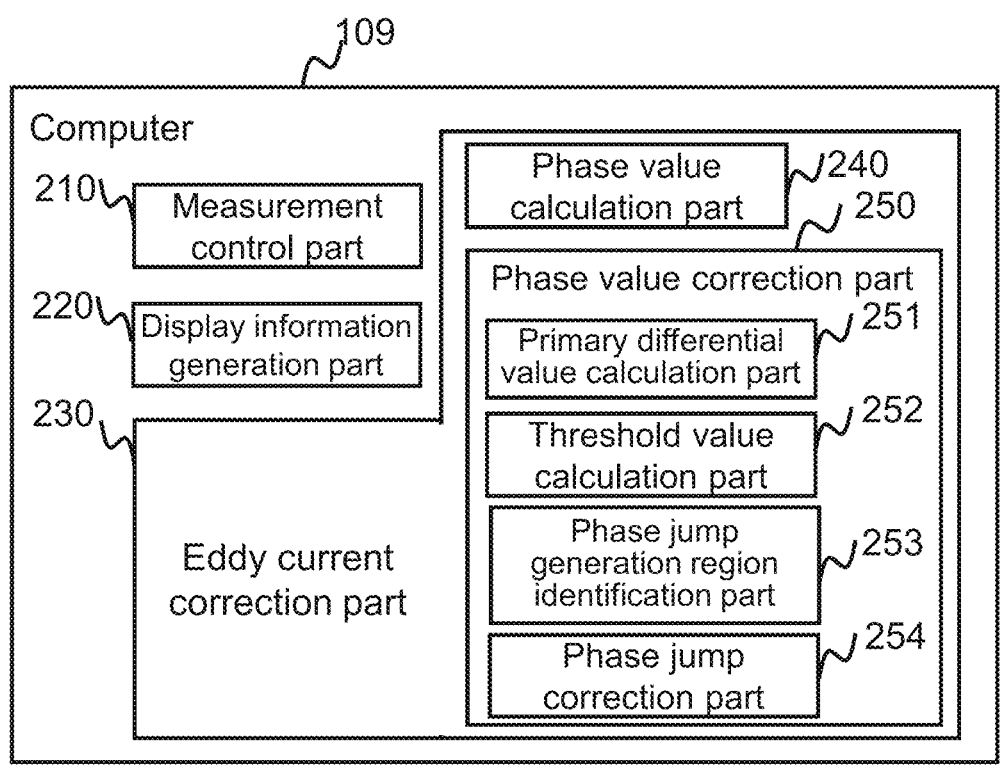
FIG. 3 is a functional block diagram of a computer provided in one embodiment of the nuclear magnetic resonance imaging device according to the present invention.

Hereafter, functions realized by the computer 109 of this embodiment will be explained. FIG. 3 is a functional block diagram of the computer 109 of this embodiment. The computer 109 of this embodiment is provided with a measurement control part 210, a display information generation part 220, and an eddy current correction part 230. The measurement control part 210 makes the sequence control device 114 to operate according to a pulse sequence and controls the parts to perform the measurement to obtain magnetic resonance signals. According to this embodiment, for example, a magnetic resonance signal of a desired metabolite is obtained for every measurement point. The eddy current correction part 230 performs eddy current correction of the magnetic resonance signals obtained by the measurement for correcting spectral distortion induced by eddy currents. The display information generation part 220 performs various kinds of processings for the magnetic resonance signals obtained after the correction of the spectral distortion induced by eddy currents, and generates display information including image information, spectrum information, and so forth.

The eddy current correction part 230 corrects spectral distortion induced by eddy currents using phase values of FID signals (free induction decay signals, henceforth referred to as signals for eddy current correction) of a substance showing larger signal intensity compared with metabolites (substance for correction, water in this embodiment). For this correction, the phase values corrected by phase jump correction are used. Therefore, the eddy current correction part 230 of this embodiment is provided with a phase value calculation part 240 for calculating a phase value from a signal for eddy current correction, and a phase value correction part 250 for correcting a phase jump in a phase value to give a corrected phase value.

The various kinds of the functions realized by the computer 9 are realized by CPU by loading programs stored in the storage device and executing them. Further, among various kinds of the functions realized by the computer 9, at least one of them may be realized by an information processor independent from the MRI device 100, which can transmit and receive data to and from the MRI device 100.

Figure 4:
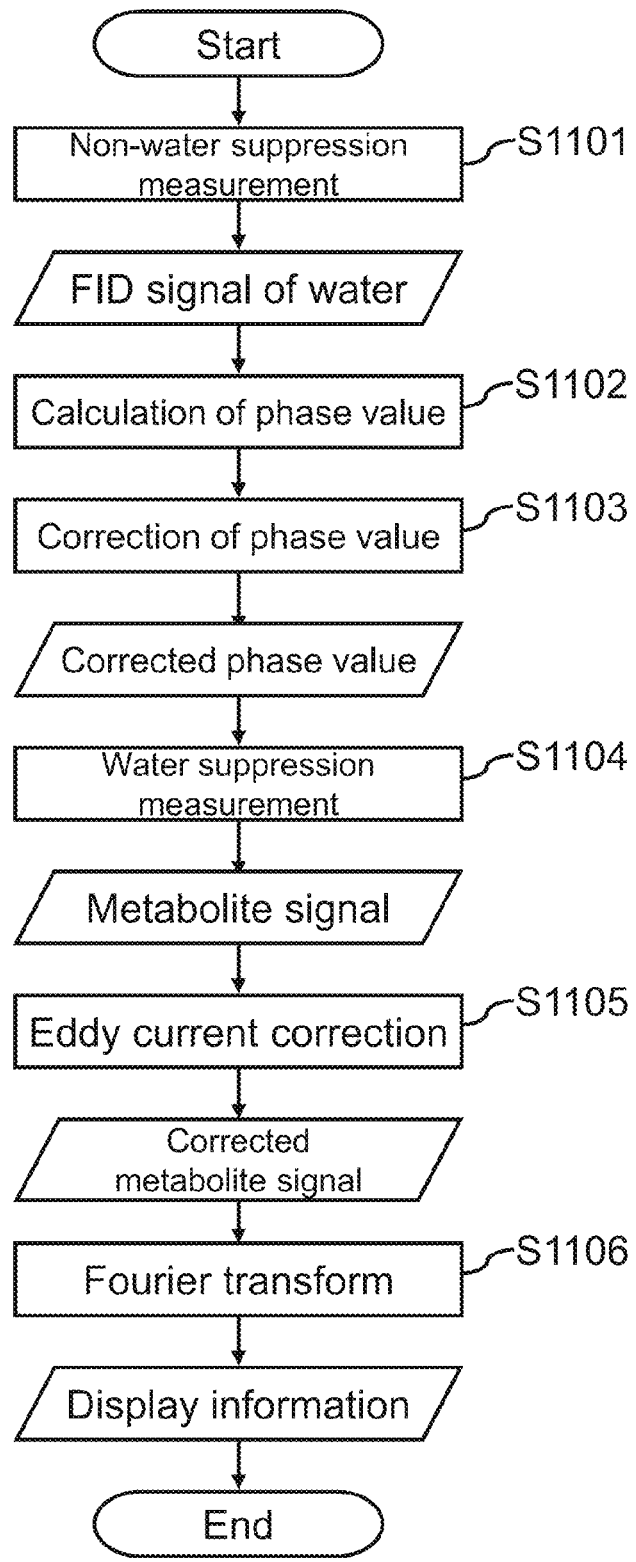
FIG. 4 is a flowchart for explaining flow of the whole measurement according to one embodiment of the present invention.

Flow of the whole measurement according to this embodiment performed by the aforementioned functions will be briefly explained below. FIG. 4 is a flowchart for explaining the flow of the whole measurement according to this embodiment.

According to this embodiment, the FID signals of water are used as signals for eddy current correction. Therefore, the measurement control part 210 first controls the sequence control device 14 according to a pulse sequence defined beforehand to perform non-water suppression measurement (Step S1101) to obtain FID signals $F(t_n)$ (n=0, . . . N−1) of water. N is a number of sampling, and $t_n$ is a discrete value representing time at the n-th measurement point. $t_0$ represents the measurement start time.

The phase value calculation part 240 calculates a phase value $\Phi(t_n)$ of the FID signals of water for every measurement point from the obtained FID signals $F(t_n)$ of water (Step S1102). The phase values $\Phi(t_n)$ of the FID signals of water are calculated from the measured FID signals $F(t_n)$ of water according to the following equation (1).

$$\Phi(t_n)=\tan^{-1}(Im(F(t_n)))/(Re(F(t_n))) \quad (1)$$

In the equation, $\tan^{-1}$ is the arc tangent function, $Im(F(t_n))$ represents an imaginary part of the complex number $F(t_n)$, and $Re(F(t_n))$ represents a real part of the complex number $F(t_n)$.

Further, the phase value correction part 250 corrects a phase jump of the phase value $\Phi(t_n)$ to give a corrected phase value $\Phi c(t_n)$, which is a phase value obtained after the correction (Step S1103).

Then, the measurement control part 210 controls the sequence control device 14 according to the pulse sequence defined beforehand to perform water suppression measurement (Step S1104) and thereby obtain metabolite signals $S(t_n)$.

Then, the eddy current correction part 230 performs eddy current correction for correcting the obtained metabolite signals $S(t_n)$ with the corrected phase values $\Phi c(t_n)$ (Step S1105) to obtain metabolite signals $S_{ecc}(t_n)$ corrected by the eddy current correction. The metabolite signals $S_{ecc}(t_n)$ corrected by the eddy current correction are calculated from the metabolite signals $S(t_n)$ according to the following equation (2) by using phase values $\Phi c(t_n)$ of the FID signals of water corrected by the phase jump correction.

$$S_{ecc}(t_n)=S(t_n)\cdot\exp(-i\cdot\Phi c(t_n)) \quad (2)$$

In the equation, i is the imaginary unit.

The display information generation part 220 carries out the Fourier transform of the metabolite signals $S_{ecc}(t_n)$ corrected by the eddy current correction to obtain a spectrum or distribution image of the metabolite (Step S1106).

An example of the pulse sequence used by the measurement control part 210 for the aforementioned measurements (non-water suppression measurement of Step S1101 and water suppression measurement of Step S1104) will be explained below. The following explanation will be made for a pulse sequence for region selection type MRSI for imaging a metabolite (henceforth referred to as MRSI pulse sequence) as an example.

Figure 5:
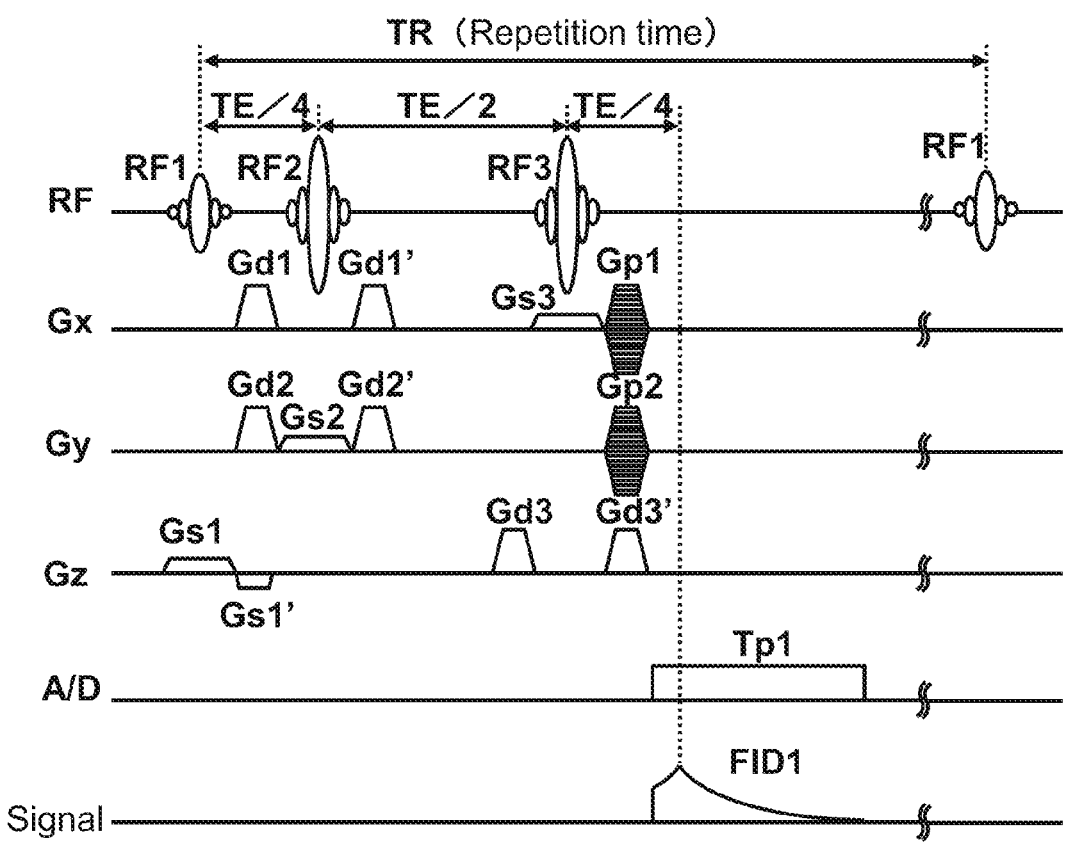
FIG. 5 shows an example of an MRSI pulse sequence according to one embodiment of the present invention.

FIG. 5 shows an example of the MRSI pulse sequence 300. In FIG. 5, RF indicates application timing of a radio frequency magnetic field pulse. Gx, Gy, and Gz indicate application timings of the gradient magnetic field pulses of the x, y, and z directions, respectively. A/D indicates measurement period of the signal. The MRSI pulse sequence 300 shown in FIG. 5 is similar to known MRSI pulse sequences, and it utilizes one excitation pulse RF1 and two inversion pulses RF2 and RF3 to selectively excite a predetermined region of interest and thereby obtain an FID signal (free induction decay) FID1 from the region of interest.

The region excited with this MRSI pulse sequence 300 is shown in FIGS. 6A to 6C. FIGS. 6A to 6C show the scout images for positioning obtained by measurement performed in advance of the main measurement, and FIGS. 6A to 6C show a trans image 410, a sagittal image 420, and a coronal image 430, respectively. The relation between the operations of the parts and the region to be excited will be explained below with reference to FIGS. 5 and 6A to 6C.

First, the radio frequency magnetic field pulse RF1 as well as gradient magnetic field pulses Gs1 and Gs1' of the z-direction are applied to excite a section 401 of the z-direction. After the time of TE/4 (TE is echo time), a radio frequency magnetic field pulse RF2 and a gradient magnetic field pulse Gs2 of the y-direction are applied. As a result, only the phase of the nuclear magnetization in the region where the section 401 of the z-direction and a section 402 of the y-direction are crossing is rephased (returned). Then, after TE/2 from the application of the radio frequency magnetic field pulse RF2, a radio frequency magnetic field pulse RF3 and a gradient magnetic field pulse Gs3 of the x-direction are applied. Only the phase of the nuclear magnetization in a region of interest 404 where the section 401 of the z-direction, the section 402 of the y-direction, and a section 403 of the x-direction are crossing is rephased, and an FID signal FID1 is generated from this region. This FID signal FID1 is measured. The gradient magnetic field pulses Gd1 to Gd3 and Gd1' to Gd3' of the three directions are the gradient magnetic field pulses for rephasing the phase of the nuclear magnetization excited by the radio frequency magnetic field pulse RF1, and dephasing the phases of the nuclear magnetization excited by RF2 and RF3. Further, after the application of the radio frequency magnetic field pulse RF3, phase encoding gradient magnetic field pulses Gp1 and Gp2 are applied. By the above procedure, a magnetic resonance signal of the region of interest 404 is obtained.

The correction of the phase value performed by the phase value correction part 250 in Step S1103 mentioned above will be explained below. The correction of the phase value of this embodiment is correction of phase jump of the phase value used for the eddy current correction. Correction of phase jump is performed by identifying a phase jump generation region in terms of the phase value, and eliminating the phase jump at that region.

In general, a temporally changing phase value has a point of inflexion at a region where a phase jump generates, and has local maximum and minimum values around that region. That is, primary time differential values (henceforth referred to as primary differential values) of phase values form a peaked curve convex upward or downward around the region where the phase jump generates. According to this embodiment, a phase jump region of the phase values is identified by using this phenomenon. That is, in terms of the primary differential values of the phase values, ranges other than this peak shape and positions thereof are extracted, and the other ranges and positions thereof are identified as phase jump generation regions.

However, regions where phase change is generated by an eddy current also show similar change. Therefore, the phase value correction part 250 of this embodiment determines whether a region where phase change has the aforementioned characteristic has that characteristic due to influence of an eddy current or due to phase jump, and identify only a region where phase change shows the aforementioned characteristic due to phase jump. In general, amount of phase change induced by an eddy current is smaller than amount of phase change induced by phase jump. Therefore, it is judged that, among phase changes, those showing a change amount smaller than a predetermined value are determined to be phase changes induced by an eddy current, and those showing a change amount not smaller than a predetermined value are determined to be phase changes induced by phase jump.

As a threshold value for determining whether a phase change has the aforementioned characteristic due to phase jump or not, there is used a phase change amount in a predetermined time domain of the primary differential values of the phase values of each measurement point. A region from the measurement start time to a predetermined time where the influence of the phase change induced by an eddy current is significant is set as the predetermined time domain. Then, phase change amount of each point of the primary differential value is calculated as an evaluation value. Regions giving such an evaluation value smaller than the threshold value are determined to be in a phase change region induced by influence of an eddy current or a phase change region induced by unevenness of static magnetic field or the like, and the other regions are determined to be in a phase jump generation region. The phase change region generated by influence of an eddy current or unevenness of static magnetic field is called a non-phase jump generation region.

The correction is performed by connecting the primary differential values of the measurement points of non-phase jump generation regions by interpolation. The corrected phase values are obtained from the connected primary differential values.

In order to realize the aforementioned processing, the phase value correction part 250 is provided with, as shown in FIG. 3, a primary differential value calculation part 251 for differentiating the phase value with time to obtain a primary differential value, a threshold value calculation part 252 for calculating the threshold value for identifying a phase jump generation region from the calculated primary differential value, a phase jump generation region identification part 253 for identifying the phase jump generation region of the phase values by using the threshold value and the primary differential value, and a phase jump correction part 254 for correcting phase jump in the phase jump generation region.

The threshold value calculated by the threshold value calculation part 252 of this embodiment is a threshold value for identifying a phase jump generation region by first identifying regions where phase jump does not generate (non-phase jump generation regions) using the threshold value, and then determining the other regions to be phase jump generation regions. Therefore, the phase jump generation region identification part 253 identifies the regions showing a primary differential value not larger than the threshold value as non-phase jump generation regions in terms of the primary differential value, and the other regions as the phase jump generation regions.

The outline of the flow of the phase value correction processing of this embodiment using the aforementioned functions will be explained below. FIG. 7 is a flowchart for explaining the flow of the phase value correction processing of this embodiment.

First, the primary differential value calculation part 251 calculates a primary differential value $\Phi z'(t_n)$ from the phase value $\Phi(t_n)$ of the FID signal of water calculated by the phase value calculation part 240 (Step S1201).

Then, the threshold value calculation part 252 calculates the threshold value $P_{th}$ used for identifying the non-phase jump generation region on the basis of the primary differential value $\Phi z'(t_n)$ (Step S1202).

Then, the phase jump generation region identification part 253 identifies the non-phase jump generation regions in terms of the primary differential values $\Phi z'(t_n)$ by using the threshold value $P_{th}$, and identifies the other regions as the phase jump generation regions PJ (Step S1203).

Finally, the phase jump correction part 254 removes the phase jump generation regions PJ in terms of the primary differential values $\Phi z'(t_n)$, connects the gaps by interpolation, and obtains phase values again from the primary differential values to correct the phase jump (Step S1204). The phase value correction part 250 thereby gives corrected phase values $\Phi c(t_n)$.

The details of the aforementioned processings will be explained below.

First, the calculation of the primary differential values performed by the primary differential value calculation part 251 in Step S1201 mentioned above will be explained. The primary differential value calculation part 251 first performs a phase aliasing connection processing for the phase values $\Phi(t_n)$ calculated by the phase value calculation part 240 to obtain phase values $\Phi z(t_n)$ after the phase aliasing connection processing. Then, the primary differential value calculation part 251 differentiates the phase values $\Phi z(t_n)$ obtained through the phase aliasing connection processing with time to obtain a primary differential function $\Phi z'(t_n)$.

Figure 8:
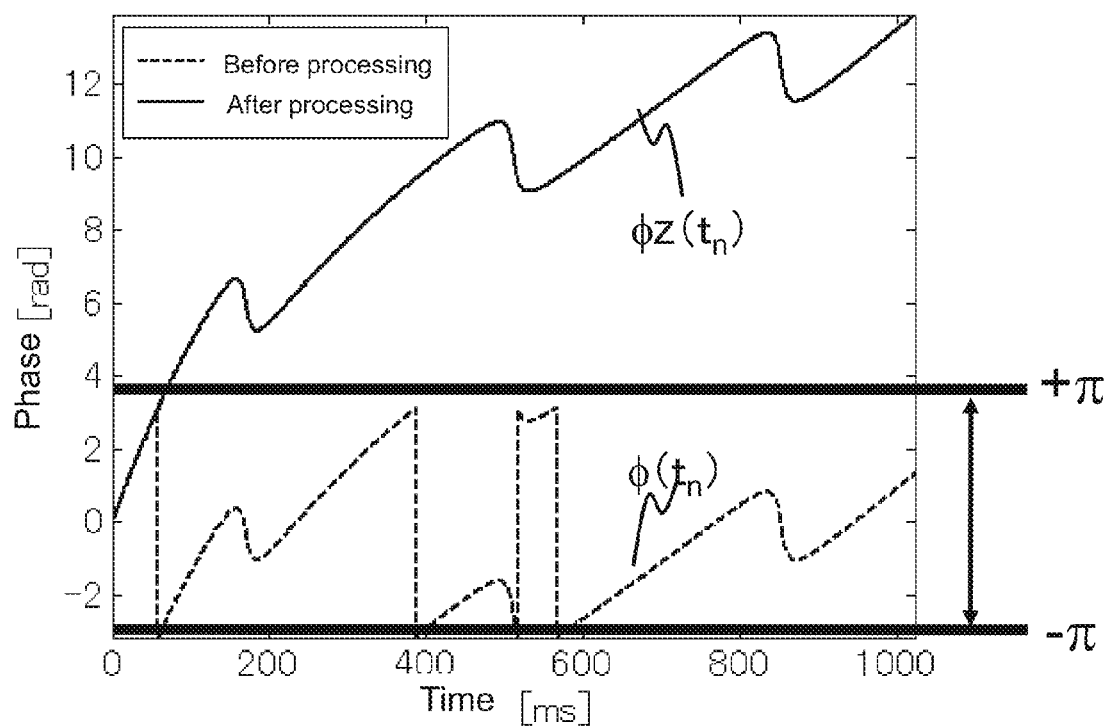
FIG. 8 is a drawing for explaining an example of a phase aliasing connection processing according to one embodiment of the present invention.

The aforementioned phase aliasing connection processing will be explained below with reference to FIG. 8. In FIG. 8, the horizontal axis indicates time from the start of the measurement of the FID signals of water (ms), and the vertical axis indicates phase value (rad). Further, the broken line indicates results of plotting of the phase values $\Phi(t_n)$ calculated from the measurement results, and the solid line indicates results of plotting of the phase values $\Phi z(t_n)$ obtained after the phase aliasing connection processing.

The phase values $\Phi(t_n)$ are calculated as a value between $-\pi$ and $+\pi$. However, a value beyond the range of $-\pi$ to $+\pi$ is generated for the phase of the FID signal of water obtained with the aforementioned MRSI pulse sequence 300. Such a phase giving a phase value out of the range of $-\pi$ to $+\pi$ is folded so that the phase value is between $-\pi$ and $+\pi$. As shown with the broken line shown in FIG. 8, the curve of the value becomes discontinuous at the folded part. Therefore, the phase aliasing connection processing for eliminating such discontinuous temporal change of the phase value is performed to obtain phase values $\Phi z(t_n)$ representing the original state of the phase change.

As the phase aliasing connection processing, various kinds of existing phase aliasing connection processings can be used. In this processing, in order to prevent phase fluctuation induced by noises, smoothing may be optionally performed. Hereafter, the phase value $\Phi z(t_n)$ obtained after the phase aliasing connection processing is referred to simply as phase value $\Phi z(t_n)$ in this specification.

The calculation of the threshold value $P_{th}$ performed by the threshold value calculation part 252 in Step S1202 will be explained below. The threshold value $P_{th}$ is used for identifying measurement points corresponding to the non-phase jump generation region in terms of the primary differential value $\Phi z'(t_n)$. The threshold value calculation part 252 calculates the threshold value $P_{th}$ used for this identification.

The threshold value calculation part 252 sets a time range where the influence of the phase change induced by an eddy current is significant as a threshold value calculation region R on the basis of the primary differential values $\Phi z'(t_n)$ of the phase values $\Phi z(t_n)$. Then, the phase change amount in the threshold value calculation region R is considered as the phase change induce by an eddy current, and is calculated as the threshold value $P_{th}$.

As described above, the influence of an eddy current is significant from the measurement start time to a predetermined time. Therefore, the threshold value calculation part 252 sets the time range from the measurement start time to the predetermined time as the threshold value calculation region R in terms of the primary differential value $\Phi z'(t_n)$ of the phase value $\Phi z(t_n)$. Then, an absolute value of the difference (M−m) of the maximum value M and the minimum value m of the primary differential values $\Phi z'(t_n)$ in the threshold value calculation region R, i.e., |(M−m)|, is set as the threshold value $P_{th}$.

The threshold value calculation region R is determined by using, for example, absolute values of FID signals $F(t_n)$ of water signals, $|F(t_n)|$. In this case, for example, a time range starting from the measurement start time in which the absolute value $|F(t_n)|$ is not smaller than a predetermined value is set as the threshold value calculation region R.

Figure 9:
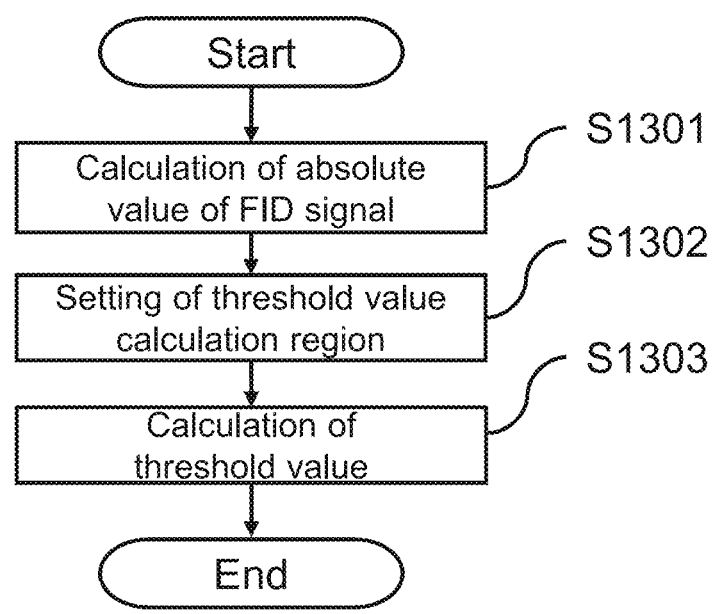
FIG. 9 is a flowchart of a threshold value calculation processing according to one embodiment of the present invention.
Figure 10A:
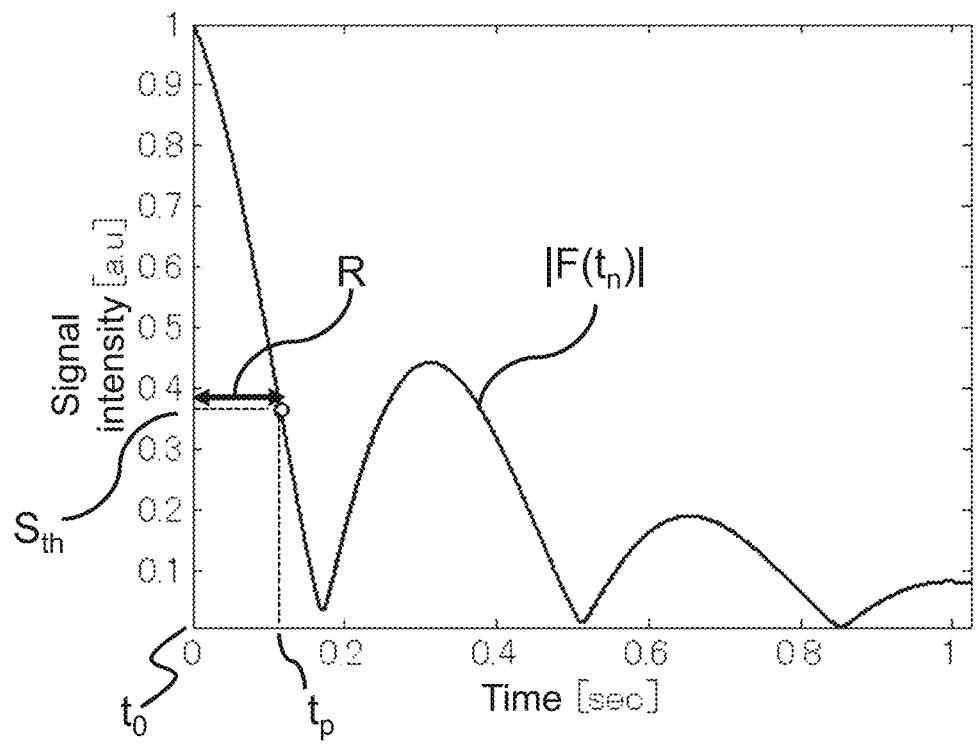
FIG. 10A is an explanatory drawing for explaining a method for determining a threshold value calculation region according to one embodiment of the present invention.
Figure 10B:
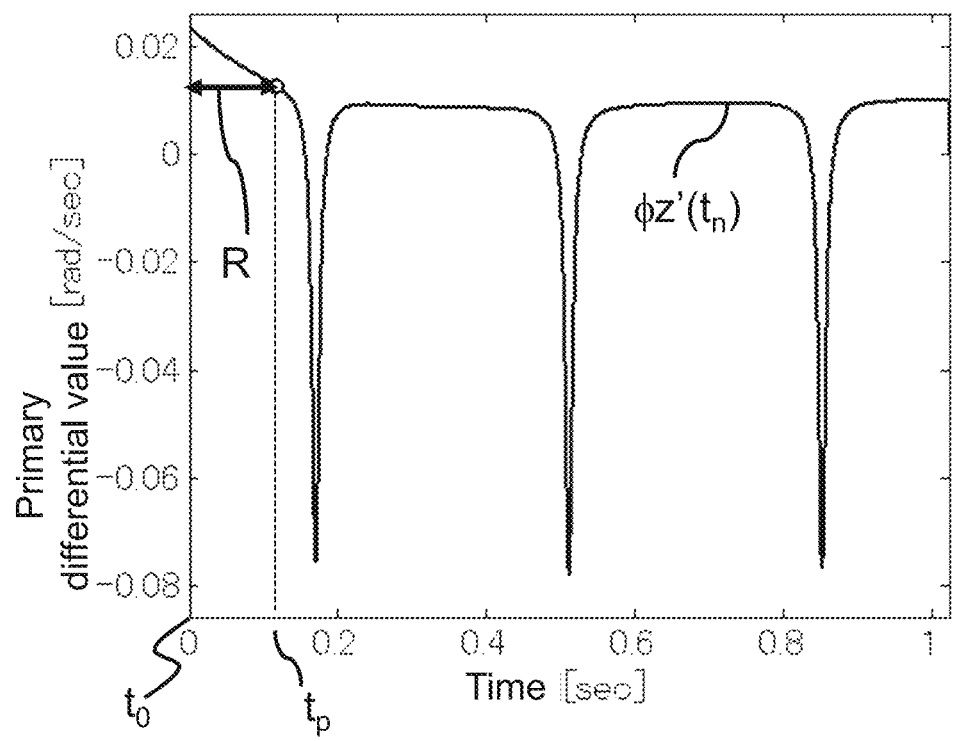
FIG. 10B is an explanatory drawing for explaining a method for determining a threshold value according to one embodiment of the present invention.

The threshold value calculation processing performed by the threshold value calculation part 252 in the case of determining the region by using the absolute values $|F(t_n)|$ will be explained. FIG. 9 shows a process flow for explaining the flow of threshold value calculation processing. FIG. 10A is an explanatory drawing for explaining a processing for determining the threshold value calculation region R from result of plotting of the absolute values $|F(t_n)|$ of the signal intensities $F(t_n)$ of the FID signals of water, and FIG. 10B is an explanatory drawing for explaining a processing for determining the threshold value $P_{th}$ using result of plotting of primary differential values $\Phi z'(t_n)$.

First, the threshold value calculation part 252 calculates absolute values $|F(t_n)|$ of signal intensities of the FID signals of water $F(t_n)$ (Step S1301). As shown in FIG. 10A, the absolute value $|F(t_n)|$ of the signal intensity of the FID signal of water $F(t_n)$ linearly decreases from the measurement start time $t_0$ to the predetermined time.

Then, as shown in FIG. 10A, the threshold value calculation part 252 identifies the first time $t_p$ (p is an integer satisfying $1 \leq p \leq N$) among the time points giving values $|F(t_n)|$ closest to the threshold value $S_{th}$ set beforehand, and set the time range from the measurement start time $t_0$ to the time $t_p$ as the threshold value calculation region R (Step S1302). According to this embodiment, the absolute value intensity $|F(T2^*)|$ at the apparent transverse magnetization relaxation time $T2^*$ is used as the threshold value $S_{th}$. Specifically, if the signal intensity of the FID signal of water when the time t is 0 (t=0) is represented as $|F(0)|$, a value satisfying the following equation (3) is used as the threshold value $S_{th}$.

$$S_{th}=|F(T2^*)|=|F(0)\times\exp(-1)| \quad (3)$$

Then, as shown in FIG. 10B, the threshold value calculation part 252 extracts the maximum value M and the minimum value m of the primary differential value $\Phi z'(t_n)$ among those for the measurement points $t_n$ within the threshold value calculation region R set in Step S1302, and calculates absolute value of the difference of the maximum value M and the minimum value m (M−m), i.e., |M−m|. Then, the obtained absolute value |M−m| is set as the threshold value $P_{th}$ (Step S1303).

The absolute value |M−m|, which is the change amount of the primary differential value $\Phi z'(t_n)$ obtained in the threshold value calculation region R, is considered to be the change amount given by an eddy current. According to this embodiment, a change amount of the primary differential value $\Phi z'(t_n)$ within a predetermined range and smaller than the above change amount given by an eddy current is judged to be phase change amount given by change of magnetic field, and the other change amounts are judged to be the change amounts given by phase jump.

The threshold value calculation region (time range) R may be determined by directly setting the predetermined time $t_p$, not using signal intensity of the FID signal of water $F(t_n)$. The predetermined time $t_p$ to be set is determined by, for example, identifying a period where an eddy current component is maintained on the basis of an experientially known time constant of eddy current. $t_p$ is determined to be, for example, several tens to several hundreds of milliseconds.

In addition, the method for determining the threshold value calculation region (time range) R is not limited to the method explained above. Any method can be used so long as a region where there is sufficient information on eddy current, and there is no change induced by phase jump can be set as the threshold value calculation region (time range) R.

Further, the threshold value $P_{th}$ may be calculated from the primary differential value $\Phi z'(t_n)$, without using the threshold value calculation region R. The primary differential values $\Phi z'(t_n)$ shown in FIG. 10B are divided into those of a plurality of small regions for the time direction. For each small region, the standard deviation of the primary differential values $\Phi z'(t_n)$ included in the small region is calculated. Among the standard deviations calculated for the small regions, the minimum standard deviation is determined. Then, the minimum standard deviation is multiplied with a predetermined coefficient to obtain the threshold value. The threshold value calculated by the above procedure uses a region where the phase change in terms of the primary differential value $\Phi z'(t_n)$ is moderate as the standard of the non-phase jump generation part. However, the evaluation value calculation region $RE_k$ explained later is determined by the aforementioned determination method for the threshold value calculation region (time range) R.

Hereafter, the method for identifying the phase jump generation region PJ performed by the phase jump generation region identification part 253 in Step S1203 will be explained. The phase jump generation region identification part 253 according to this embodiment judges whether every measurement point $t_n$ is a non-phase jump generation region. The judgment is performed by comparing an evaluation value $E_k$ with the threshold value $P_{th}$ calculated by the threshold value calculation part 252 for every measurement point $t_k$ as the object of the judgment. When the evaluation value $E_k$ is smaller than the threshold value $P_{th}$, the measurement point $t_k$ as the object of the judgment is judged to be a non-phase jump generation region. The evaluation value $E_k$ is the absolute value $|(M_k-m_k)|$ of the difference $(M_k-m_k)$ of the maximum value $M_k$ and the minimum value $m_k$ among the primary differential values $\Phi z'(t_n)$ included in the evaluation value calculation region $RE_k$ having a predetermined time width and a center at the measurement point $t_k$.

FIG. 11 is a flowchart showing the flow of the processing performed by the phase jump generation region identification part 253.

The phase jump generation region identification part 253 first sets the first measurement point $t_k$ (k is an integer of 1 or larger) (Step S1401). The measurement point for which whether it is a non-phase jump generation region or not is judged is henceforth called an evaluation point. According to this embodiment, the measurement time (measurement point) $t_{p+1}$ next to the time $t_p$ calculated by the threshold value calculation part 252 is set to be the first evaluation point $t_k$.

Then, the phase jump generation region identification part 253 sets the evaluation value calculation region $RE_k$ corresponding to the evaluation point $t_k$ (Step S1402). According to this embodiment, the same range as the threshold value calculation region R having the center at the evaluation point $t_k$ is set as the evaluation value calculation region $RE_k$. Therefore, the evaluation value calculation region $RE_k$ corresponding to the evaluation point $t_k$ is set as a range of from $t_k-R/2$ to $t_k+R/2$.

Then, the phase jump generation region identification part 253 calculates the evaluation value $E_k$ of the evaluation point $t_k$ (Step S1403). According to this embodiment, the maximum value $M_k$ and the minimum value $m_k$ of the primary differential values $\Phi z'(t_n)$ of the measurement points $t_n$ in the evaluation value calculation region $RE_k$ are calculated. Further, the absolute value $|M_k-m_k|$ of the difference of the maximum value $M_k$ and the minimum value $m_k$ is calculated as the evaluation value $E_k$.

Then, the phase jump generation region identification part 253 compares the calculated evaluation value $E_k$ and the threshold value $P_{th}$ (Step S1404), and if the evaluation value $E_k$ is not larger than the threshold value $P_{th}$, it is judged that the evaluation point $t_k$ is a non-phase jump generation point where phase jump is not generated (Step S1406). That is, it is judged that, at this evaluation point $t_k$, only a linear phase change is generated due to unevenness of the static magnetic field, or only a phase change is generated by an eddy current. On the other hand, if the evaluation value $E_k$ is larger than the threshold value $P_{th}$, the evaluation point $t_k$ is judged to be a phase jump generation point (Step S1405). That is, it is judged that, at this evaluation point $t_k$, phase jump is generated.

The above steps are repeated in the above order for all the evaluation points $t_k$ after $t_{p+1}$ (Steps S1407 and S1408). The phase jump generation region identification part 253 thereby judges whether every measurement point $t_k$ is the phase jump generation point or the non-phase jump generation point. Continuous phase jump generation points are called a phase jump generation region, and continuous non-phase jump generation points are called a non-phase jump generation region.

Figure 12:
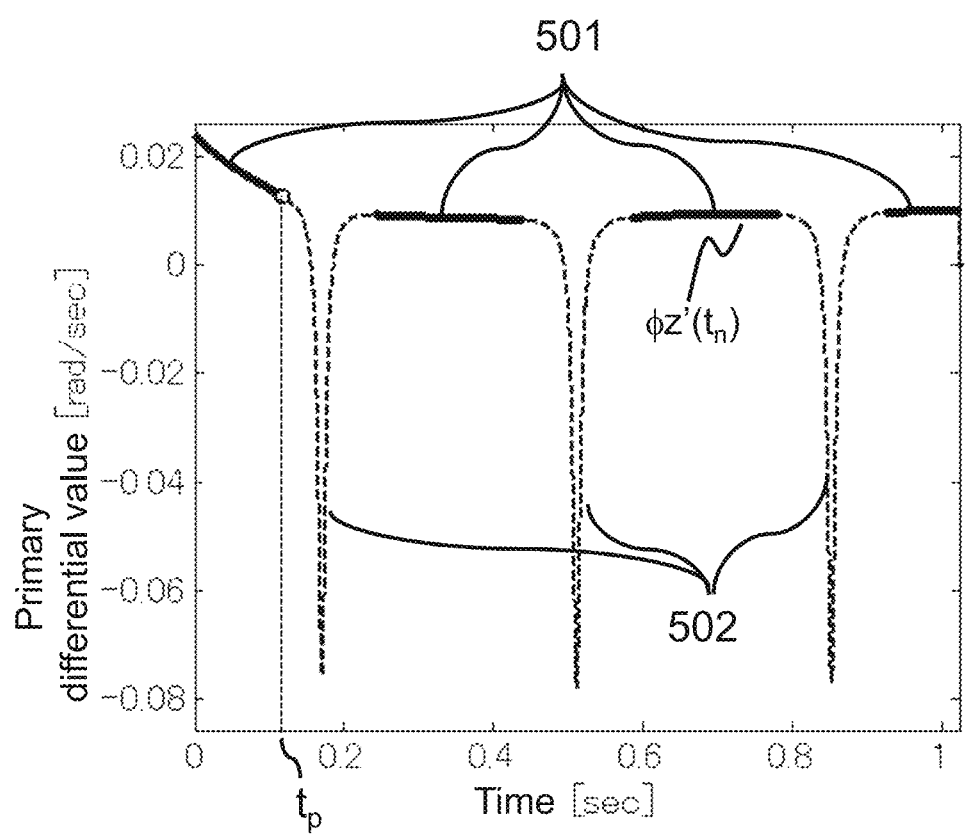
FIG. 12 is an explanatory drawing for explaining a phase jump correction region identification processing according to one embodiment of the present invention.

The result of the judgment performed by the phase jump generation region identification part 253 of this embodiment is shown in FIG. 12. In FIG. 12, the horizontal axis indicates time from the start of measurement of the FID signals of water (sec), and the vertical axes indicates the primary differential value $\Phi z'(t_n)$ of the phase of the FID signal of water (rad/sec). In FIG. 12, the solid lines 501 indicate groups of the primary differential values $\Phi z'(t_n)$ of the non-phase jump generation regions, and the broken lines 502 indicate groups of the primary differential values $\Phi z'(t_n)$ of the phase jump generation regions. In FIG. 12, the white circle corresponds to the aforementioned $t_p$.

As described above, the phase jump generation region identification part 253 of this embodiment identifies the phase jump generation region by using the primary differential values $\Phi z'(t_n)$ of the phases of the FID signals of water.

Figure 13:
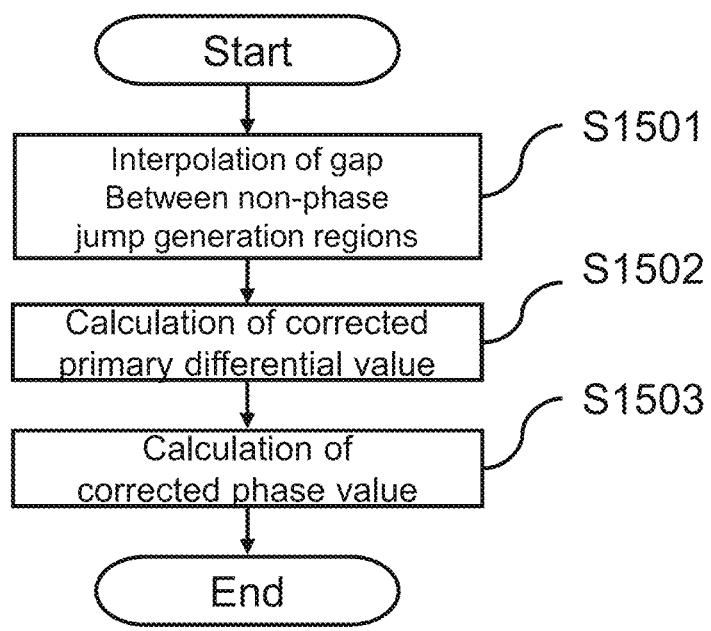
FIG. 13 is a flowchart of a phase jump correction processing according to one embodiment of the present invention.

Hereafter, the phase jump correction performed by the phase jump correction part 254 in Step S1204 mentioned above will be explained. FIG. 13 shows a flowchart for explaining the flow of the phase jump correction performed by the phase jump correction part 254 of this embodiment.

Figure 14:
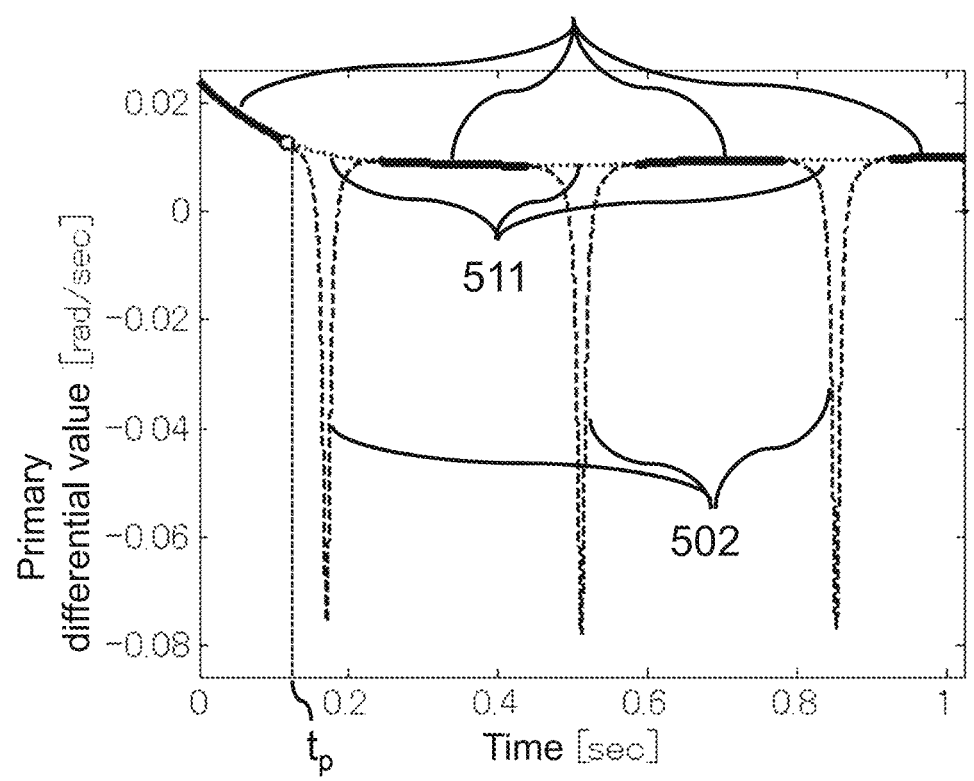
FIG. 14 is an explanatory drawing for explaining phase jump correction according to one embodiment of the present invention.

First, the phase jump correction part 254 connects adjacent non-phase jump generation regions 501 by interpolation on the result of plotting of the primary differential values $\Phi z'(t_n)$ (Step S1501). Specifically, as shown in FIG. 14, the interpolation is performed so that the non-phase jump generation regions 501 are smoothly connected on the result of plotting of the primary differential values $\Phi z'(t_n)$, and the primary differential values $\Phi z'(t_n)$ of the phase jump generation regions 502 are removed. For the interpolation, there are used known methods such as linear interpolation, which connects the ends of the adjacent non-phase jump generation regions 501 with a straight line, spline interpolation, and cubic interpolation.

The phase jump correction part 254 performs fitting of the interpolated plotting result 511 to give a phase jump-corrected primary differential function $\Phi c'(t_n)$ and phase jump-corrected primary differential values $\Phi c'(t_n)$ as the values (511) of the function for the measurement points (Step S1502). The fitting is performed by using a polynomial, an exponential function, or the like.

Then, the phase jump correction part 254 gives corrected phase values $\Phi c(t_n)$ from the corrected primary differential values $\Phi c'(t_n)$ (Step S1503). In this processing, for example, by integrating the corrected primary differential function $\Phi c'(t)$, a phase jump-corrected phase function $\Phi c(t)$ is obtained, and phase jump-corrected phase values $\Phi c(t_n)$ are calculated as values of the corrected phase function $\Phi c(t)$ for the every measurement point $t_n$.

The corrected phase values $\Phi c(t_n)$ may be calculated as a power sum of the corrected primary differential values $\Phi c'(t_n)$.

Figure 15:
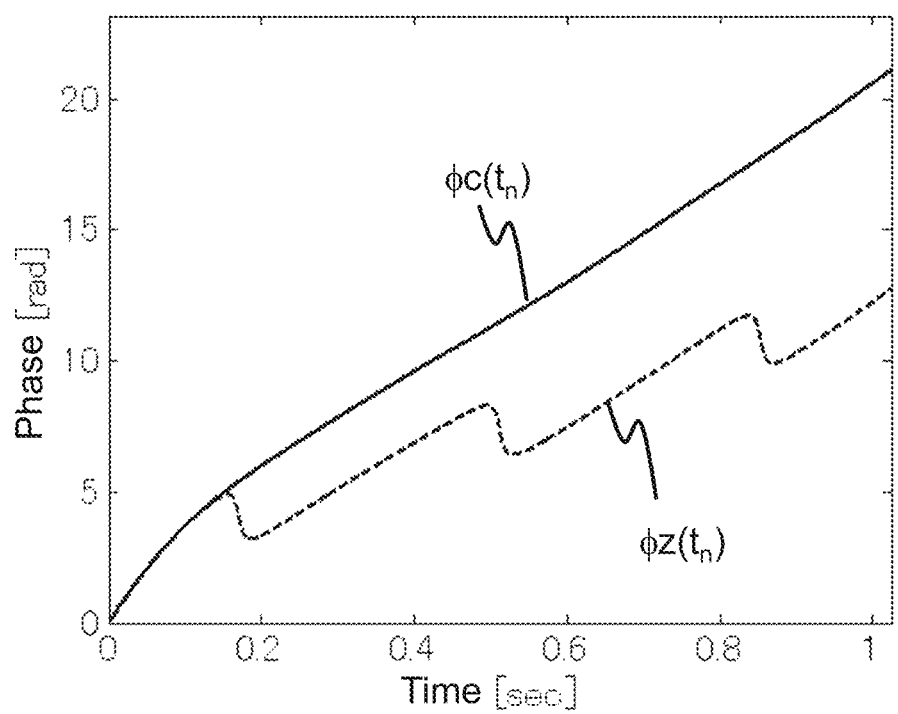
FIG. 15 is a graph of the phase values obtained before and after carrying out the phase jump correction processing according to one embodiment of the present invention.

An exemplary graph of the phase values obtained before and after the phase jump correction performed by the aforementioned phase jump correction part 254 is shown in FIG. 15. In this graph, the horizontal axis indicates time (sec), and the vertical axis indicates phase (rad). The broken line represents the result of plotting of the phase values $\Phi z(t_n)$ of the FID signals of water before the phase jump correction (graph of the phase function $\Phi z(t)$), and the solid line represents the result of plotting of the phase jump-corrected phase values $\Phi c(t_n)$ of the FID signals of water (graph of the phase function $\Phi c(t)$). As shown in this graph, it can be seen that the phase jumps of the FID signals of water are eliminated by the aforementioned phase jump correction processing.

As explained above, the magnetic resonance imaging device of this embodiment is the magnetic resonance imaging device 100 comprising the static magnetic field application part for applying a static magnetic field to a subject, the gradient magnetic field application part for applying a gradient magnetic field to the subject, the radio frequency magnetic field pulse irradiation part for irradiating a radio frequency magnetic field pulse on the subject, the reception part for receiving magnetic resonance signals generated from the subject, and the control part, wherein the control part comprises the measurement control part 210 for controlling operations of the gradient magnetic field application part, the radio frequency magnetic field pulse irradiation part, and the reception part to obtain a magnetic resonance signal of a desired metabolite for every measurement point, the eddy current correction part 230 for performing eddy current correction of the magnetic resonance signal, and the display information generation part 220 for generating display information from the magnetic resonance signal for every measurement point corrected by the eddy current correction part 230, the eddy current correction part 230 comprises the phase value calculation part 240 for calculating a phase value of an FID signal of a substance for correction showing a larger signal intensity compared with a metabolite as a measurement object for every measurement point, and the phase value correction part 250 for correcting a phase jump of the phase value to obtain a corrected phase value, the phase value correction part 250 comprises the primary differential value calculation part 251 for calculating a primary time differential value of the phase value for every measurement point, the threshold value calculation part 252 for calculating a threshold value for identifying a phase jump generation region where a phase jump is generated, the phase jump generation region identification part 253 for identifying the phase jump generation region of the phase value using the threshold value and the primary time differential value, and the phase jump correction part 254 for correcting the phase jump of the phase value by correcting the primary time differential value of the phase jump generation region, and the eddy current correction part 230 performs the eddy current correction by using the phase jump-corrected phase value.

The threshold value calculation part 252 may set a predetermined region as a threshold value calculation region, and may calculate an absolute value of a difference of the maximum value and the minimum value of the primary time differential values in the threshold value calculation region as the threshold value. The threshold value calculation region may be a region from a measurement start time to a predetermined time. The predetermined time may be a time when absolute value of signal intensity of the FID signal of the substance for correction first becomes the predetermined value.

The threshold value calculation part 252 may divide a sequence of the primary time differential values into a plurality of small regions in the direction of time, calculate standard deviation of the primary time differential values included in each small region for every small region, identifies the smallest standard deviation out of all the calculated standard deviations, and calculate a value corresponding to the identified smallest standard deviation multiplied with a predetermined coefficient as the threshold value.

Further, the phase jump generation region identification part 253 may calculate an absolute value of a difference of the maximum value and the minimum value of the primary time differential values included in the evaluation value calculation region, which is a predetermined time width of which center is a predetermined evaluation point, as an evaluation value, compare the evaluation value calculated for every measurement point as the evaluation point with the threshold value, and identify measurement points at which the evaluation value is larger than the threshold value as the phase jump generation region, and the other measurement points as the non-phase jump generation region.

The phase jump correction part 254 may connect the primary time differential values of the non-phase jump generation regions by interpolation to correct the phase jump. The interpolation may be linear interpolation for connecting the primary time differential values at the ends of the adjacent non-phase jump generation regions with a straight line. Further, the phase jump correction part 254 may give a power sum of the primary time differential values obtained after the interpolation as a phase jump-corrected phase value. Further, the phase jump correction part 254 may give a value of a function obtained by integrating the primary time differential values obtained by fitting of the primary time differential values obtained after the interpolation corresponding to each measurement point as the phase jump-corrected phase value.

As described above, according to this embodiment, in the eddy current correction processing for correcting spectral distortion induced by an eddy current performed by using a phase value of an FID signal of a substance showing a larger signal intensity compared with a metabolite as an object of measurement, the eddy current correction is performed by using phase values corrected for phase jump (phase jump-corrected phase value).

The phase values corrected for phase jump are obtained by removing phase jump generation regions identified by using primary differential values of phase values in terms of the primary differential values. That is, the corrected phase values are obtained as a power sum of the interpolated primary differential values obtained by interpolating gaps between the primary differential values of measurement points other than measurement points identified as phase jump generation regions.

The phase jump generation region is identified as a region where the phase changes in a degree larger than a predetermined threshold value within a predetermined range by using a primary differential value. For example, a time range influenced by an eddy current is identified by using signal intensity of the signal for eddy current correction, then, from the change amount of the phase value of the signal for eddy current correction in the range, the change amount of the phase value given by an eddy current is identified as the threshold value $P_{th}$, and an evaluation unit R is determined. Then, by using these, the primary differential values of the phase values are evaluated to identify a phase jump generation region.

Therefore, according to this embodiment, a phase jump generation region can be identified regardless of the presence or absence of an extreme of the absolute value intensity of the FID signal of the object for phase value correction. Further, the identification can be performed by simple calculation. Since the region to be corrected is identified with good accuracy, accuracy of the correction is also improved.

Therefore, according to this embodiment, phase jump of a phase value used for the eddy current correction can be efficiently and accurately removed. Further, since the eddy current correction processing of magnetic resonance signals of a measurement object is performed by using the phase values corrected with good accuracy, ringing artifacts can be effectively prevented, and the spectral distortion induced by an eddy current can be favorably corrected. Therefore, high quality display information can be obtained.

Further, according to this embodiment, a baseline part is identified, and an extreme part is removed. According to the technique of Non-patent document 3, an extreme part is identified. Therefore, according to this invention, fitting processing of a region judged to have a phase jump is not required, unlike the technique of Non-patent document 3. Further, since the phase jump correction processing is carried out in terms of the primary differential value, there is not required the processing for determining phase change amount in a correction region in accordance with time change of the phase value, and performing the correction so that the corrected regions and the other regions are smoothly connected, which is used in Non-patent document 3. Therefore, processing amount can be markedly reduced, and results can be quickly obtained with little load.

The effect of the eddy current correction according to this embodiment is confirmed below by computer simulation. The results of the computer simulation are shown in FIG. 16.

Figure 16A:
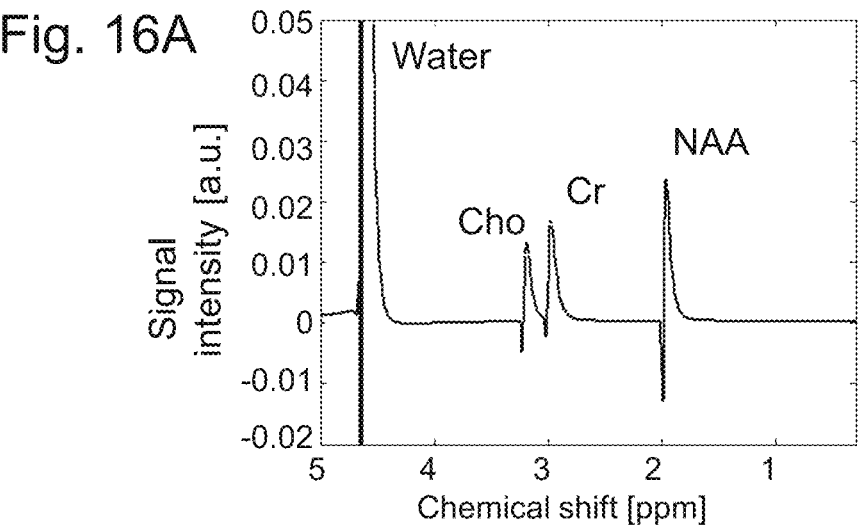
FIG. 16A is an explanatory drawing for explaining effect of one embodiment of the present invention by using computer simulation results, which is a graph of a metabolite spectrum based on the computer simulation results obtained without performing eddy current correction.
Figure 16B:
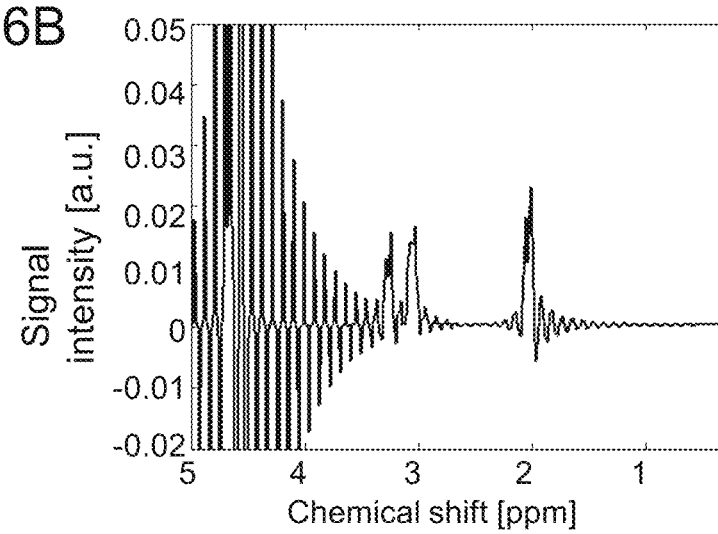
FIG. 16B is an explanatory drawing for explaining effect of one embodiment of the present invention by using computer simulation results, which is a graph of a metabolite spectrum based on the computer simulation results obtained with performing eddy current correction by using phase values not corrected by the phase jump correction according to one embodiment of the present invention.
Figure 16C:
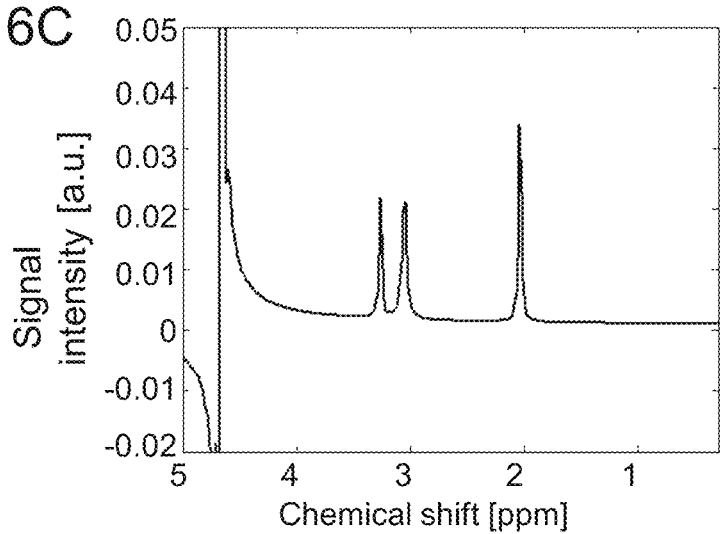
FIG. 16C is an explanatory drawing for explaining effect of one embodiment of the present invention by using computer simulation results, which is a graph of a metabolite spectrum based on the computer simulation results obtained with performing eddy current correction by using phase values corrected by the phase jump correction according to one embodiment of the present invention.
Figure 17A:
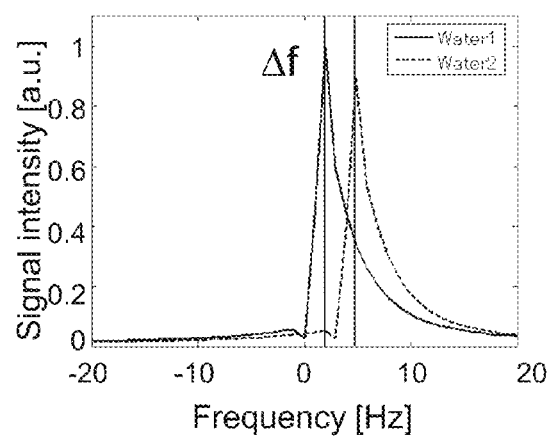
FIG. 17A is an explanatory drawing for explaining cause of generation of ringing artifacts in eddy current correction performed by using phase data of FID signals of water, which is a graph of spectrum of FID signals of water based on computer simulation.
Figure 17B:
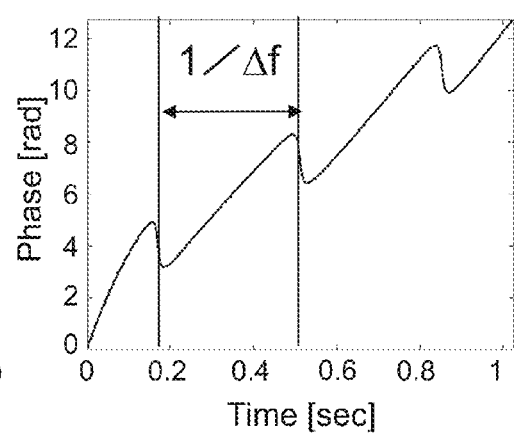
FIG. 17B is an explanatory drawing for explaining cause of generation of ringing artifacts in eddy current correction performed by using phase data of FID signals of water, which is a graph of phase values of FID signals of water shown in FIG. 17A.
Figure 17C:
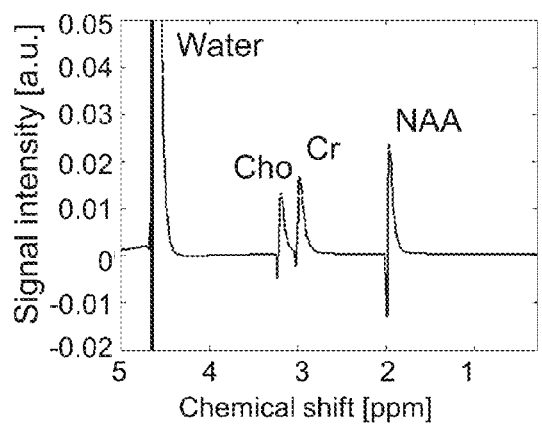
FIG. 17C is an explanatory drawing for explaining cause of generation of ringing artifacts in eddy current correction performed by using phase data of FID signals of water, which is a graph of the same spectrum obtained before the eddy current correction.
Figure 17D:
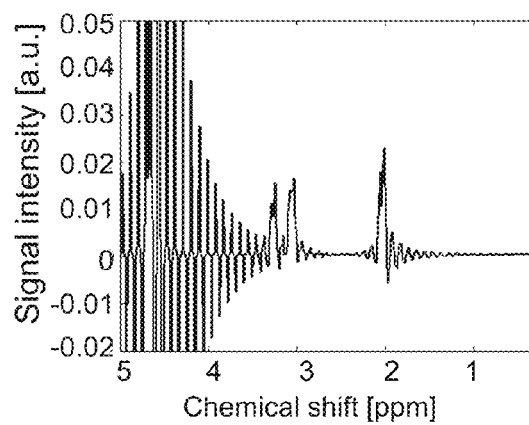
FIG. 17D is an explanatory drawing for explaining cause of generation of ringing artifacts in eddy current correction performed by using phase data of FID signals of water, which is a graph of the same spectrum obtained after the eddy current correction.

FIG. 16A shows a metabolite spectrum obtained without performing eddy current correction, FIG. 16B shows a metabolism spectrum obtained with performing eddy current correction by using phase values not corrected by the phase jump correction according to this embodiment, and FIG. 16C shows a metabolism spectrum obtained with performing eddy current correction by using phase values corrected by the phase jump correction according to this embodiment.

As shown in these spectra, it can be seen that if the eddy current correction is performed by using the phase values obtained after the phase jump correction according to this embodiment, ringing artifacts induced by phase jump can be removed, and the spectral distortion induced by an eddy current can also be corrected.

The above explanations of this embodiment are made by exemplifying a case of obtaining the phase values used for the correction of eddy current from FID signals of water. However, the present invention is not limited to such an embodiment. The signals are not particularly limited to FID signals of water, and may be signals of a substance showing larger signal intensity compared with a metabolite as an object of measurement.

DENOTATION OF REFERENCE NUMERALS

100: MRI device, 101: subject, 102: static magnetic field generation magnet, 103: gradient coil, 104: shim coil, 105: transmission coil, 106: receiver coil, 107: transmitter, 108: receiver, 109: computer, 110: display, 111: external storage device, 112: power supply part for gradient magnetic field, 113: power supply part for shim, 114: sequence control device, 115: input device, 120: MRI device, 130: MRI device, 210: measurement control part, 220: display information generation part, 230: eddy current correction part, 240: phase value calculation part, 250: phase value correction part, 251: primary differential value calculation part, 252: threshold value calculation part, 253: phase jump generation region identification part, 254: phase jump correction part, 300: MRSI pulse sequence, 401: section, 402: section, 403: section, 404: region of interest, 410: trans image, 420: sagittal image, 430: coronal image, 501: non-phase jump generation region, 502: phase jump generation region, 511: plotting result obtained after interpolation

The invention claimed is:

1. A magnetic resonance imaging device comprising:
a static magnetic field application part for applying a static magnetic field to a subject;
a gradient magnetic field application part for applying a gradient magnetic field to the subject;
a radio frequency magnetic field pulse irradiation part for irradiating a radio frequency magnetic field pulse on the subject;
a reception part for receiving magnetic resonance signals generated from the subject; and
a control part;
wherein the control part comprises:
a measurement control part for controlling operations of the gradient magnetic field application part, the radio frequency magnetic field pulse irradiation part, and the reception part to obtain a magnetic resonance signal of a desired metabolite for every measurement point,
an eddy current correction part for performing eddy current correction of the magnetic resonance signal, and
a display information generation part for generating display information from the magnetic resonance signal for every measurement point corrected by the eddy current correction part,
wherein the eddy current correction part comprises:
a phase value calculation part for calculating a phase value of an FID signal of a substance for correction showing a larger signal intensity compared with a metabolite as a measurement object for every measurement point, and
a phase value correction part for correcting a phase jump of the phase value to obtain a corrected phase value,
wherein the phase value correction part comprises:
a primary differential value calculation part for calculating a primary time differential value of the phase value for every measurement point,
a threshold value calculation part for calculating a threshold value for identifying a phase jump generation region where a phase jump is generated,
wherein the threshold value calculation part sets a redetermined region as a threshold value calculation region and calculates an absolute value of a difference of the maximum value and the minimum value of the primary time differential values in the threshold value calculation region as the threshold value,
a phase jump generation region identification part for identifying the phase jump generation region of the phase value using the threshold value and the primary time differential value, and
a phase jump correction part for correcting the phase jump of the phase value by correcting the primary time differential value of the phase jump generation region, and
wherein the eddy current correction part performs the eddy current correction by using the phase jump-corrected phase value.

2. The magnetic resonance imaging device according to claim 1, wherein: the threshold value calculation region is a region from a measurement start time to a predetermined time.

3. The magnetic resonance imaging device according to claim 2, wherein the predetermined time is a time when absolute value of signal intensity of the FID signal of the substance for correction first becomes the predetermined value.

4. The magnetic resonance imaging device according to claim 1, wherein the threshold value calculation part divides a sequence of the primary time differential values into a plurality of small regions in the direction of time, calculates standard deviation of the primary time differential values included in each small region for every small region, identifies the smallest standard deviation out of all the calculated standard deviations, and calculates a value corresponding to the identified smallest standard deviation multiplied with a predetermined coefficient as the threshold value.

5. The magnetic resonance imaging device according to claim 1, wherein the phase jump generation region identification part calculates an absolute value of a difference of the maximum value and the minimum value of the primary time differential values included in the evaluation value calculation region, which is a predetermined time width of which center is a predetermined evaluation point, as an evaluation value, compares the evaluation value calculated for every measurement point as the evaluation point with the threshold value, and identifies measurement points at which the evaluation value is larger than the threshold value as the phase jump generation region, and the other measurement points as the non-phase jump generation region.

6. The magnetic resonance imaging device according to claim 5, wherein the phase jump correction part connects the primary time differential values of the non-phase jump generation regions by interpolation to correct the phase jump.

7. The magnetic resonance imaging device according to claim 6, wherein the interpolation is linear interpolation for connecting the primary time differential values at the ends of the adjacent non-phase jump generation regions with a straight line.

8. The magnetic resonance imaging device according to claim 6, wherein the phase jump correction part gives a power sum of the primary time differential values obtained after the interpolation as the phase jump-corrected phase value.

9. The magnetic resonance imaging device according to claim 6, wherein the phase jump correction part gives a value of a function obtained by integrating the primary time differential values obtained by fitting of the primary time differential values obtained after the interpolation corresponding to each measurement point as a phase jump-corrected phase value.

10. A phase value correction method for correcting a phase jump of a phase value in a magnetic resonance imaging device, comprising:
applying, by a static magnetic field application part, a static magnetic field to a subject,
applying, by a gradient magnetic field application part, a gradient magnetic field to the subject,
irradiating, by a radio frequency magnetic field pulse irradiation part, a radio frequency magnetic field pulse on the subject,
receiving, by a reception part, magnetic resonance signals generated from the subject,
controlling, by a measurement control part, operations of the gradient magnetic field application part, the radio frequency magnetic field pulse irradiation part, and the reception part to obtain a magnetic resonance signal of a desired metabolite for every measurement point,
performing, by an eddy current correction part, eddy current correction of the magnetic resonance signal by using a phase value of an FID signal of a substance for correction showing a larger signal intensity compared with a metabolite as a measurement object for every measurement point, and
generating, by a display information generation part, display information from the magnetic resonance signal for every measurement point corrected by the eddy current correction part, which comprises:
a primary differential value calculation step of calculating a primary time differential value of the phase value for every measurement point,
a threshold value calculation step of calculating a threshold value for identifying a phase jump generation region where a phase jump is generated,
wherein the threshold value calculation step sets a predetermined region as a threshold value calculation region and calculates an absolute value of a difference of the maximum value and the minimum value of the primary time differential values in the threshold value calculation region as the threshold value,
a phase jump generation region identification step of identifying the phase jump generation region of the phase value using the threshold value and the primary time differential value,
a phase jump correction step of correcting the phase jump of the phase value by correcting the primary time differential value of the phase jump generation region, and
a corrected phase value calculation step of obtaining a corrected phase value from the corrected primary time differential value.

11. A program for operating a computer of a magnetic resonance imaging device comprising:
a static magnetic field application part for applying a static magnetic field to a subject;
a gradient magnetic field application part for applying a gradient magnetic field to the subject;
a radio frequency magnetic field pulse irradiation part for irradiating a radio frequency magnetic field pulse on the subject;
a reception part for receiving magnetic resonance signals generated from the subject;
a measurement control part for controlling operations of the gradient magnetic field application part, the radio frequency magnetic field pulse irradiation part, and the reception part to obtain a magnetic resonance signal of a desired metabolite for every measurement point;
an eddy current correction part for performing eddy current correction of the magnetic resonance signal by using a phase value of an FID signal of a substance for correction showing a larger signal intensity compared with a metabolite as a measurement object for every measurement point; and
a display information generation part for generating display information from the magnetic resonance signal for every measurement point corrected by the eddy current correction part, as:
a primary differential value calculation part for calculating a primary time differential value of the phase value for every measurement point,
a threshold value calculation part for calculating a threshold value for identifying a phase jump generation region where a phase jump is generated,
wherein the threshold value calculation part sets a and calculates an absolute value of a difference of the maximum value and the minimum value of the primary time differential values in the threshold value calculation region as the threshold value,
a phase jump generation region identification part for identifying the phase jump generation region of the phase value using the threshold value and the primary time differential value, and
a phase jump correction part for correcting the phase jump of the phase value by correcting the primary time differential value of the phase jump generation region and obtaining a corrected phase value from the corrected primary time differential value.

* * * * *